(12) United States Patent
Sinacore et al.

(10) Patent No.: US 7,807,804 B2
(45) Date of Patent: Oct. 5, 2010

(54) METHODS AND COMPOSITIONS FOR IMPROVING RECOMBINANT PROTEIN PRODUCTION

(75) Inventors: Martin S. Sinacore, Andover, MA (US); Mark Leonard, Manchester, NH (US); Haley A. Laken, Pepperell, MA (US); Jason Rouse, Londonderry, NH (US)

(73) Assignee: Wyeth LLC, Madison, NJ (US)

( * ) Notice: Subject to any disclaimer, the term of this patent is extended or adjusted under 35 U.S.C. 154(b) by 323 days.

(21) Appl. No.: 11/244,678

(22) Filed: Oct. 5, 2005

(65) Prior Publication Data

US 2006/0099206 A1 May 11, 2006

Related U.S. Application Data

(60) Provisional application No. 60/616,474, filed on Oct. 5, 2004.

(51) Int. Cl.
*C12N 15/11* (2006.01)
(52) U.S. Cl. ...................... 536/23.1; 435/455
(58) Field of Classification Search ........................ None
See application file for complete search history.

(56) References Cited

U.S. PATENT DOCUMENTS

| | | | | |
|---|---|---|---|---|
| 6,075,181 A * | 6/2000 | Kucherlapati et al. | ......... | 800/25 |
| 6,150,141 A | 11/2000 | Jarrell | | |
| 7,122,637 B2 * | 10/2006 | Presta | ..................... | 530/387.3 |
| 2003/0165496 A1 | 9/2003 | Basi et al. | | |

FOREIGN PATENT DOCUMENTS

| WO | WO 87/02671 | 5/1987 |
|---|---|---|
| WO | WO 2005/035753 | 4/2005 |
| WO | 2006041934 A2 | 4/2006 |

OTHER PUBLICATIONS

Choi T et al., "A Generic Intron Increases Gene Expression in Transgenic Mice", *Molecular and Cellular Biology*, vol. 11, No. 6:pp. 3070-3074 (1991).
Robbins P F et al., "The Intronic Region of an Incompletely Spliced gp100 Gene Transcript Encodes an Epitope Recognized by Melanoma-Reactive Tumor-Infiltrating Lymphocytes", *Journal of Immunology*, vol. 159, No. 1:pp. 303-308 (1997).
Ward S B et al., "Spontaneous deletions in Ig heavy chain genes: flanking sequences influence splice site selection", *Nucleic Acids Research*, vol. 19, No. 23:pp. 6475-6480 (1991).
Myers K A et al., "Targeting immune effector molecules to human tumor cells through genetic delivery of 5T4-specific scFv fusion proteins" *Cancer Gene Therapy*, vol. 9, No. 11:pp. 884-896 (2002).
Neuberger M S et al., "The intron requirement for immunoglobulin gene expression is dependent upon the promoter", *Nucleic Acids Research*, vol. 16, No. 14:pp. 6713-6724 (1988).
Buchman A R et al., "Comparison of Intron-Dependent and Intron-Independent Gene Expression" *Molecular and Cellular Biology*, vol. 8, No. 10:pp. 4395-4405 (1988).
Nott A et al., "A quantitative analysis of intron effects on mammalian gene expression", *RNA*, vol. 9:pp. 607-617 (2003).
"Nucleotide sequence of a variable heavy chain of IgG4", *Geneseq Database Accession No. ADZ51216*, 2 pages (Jun. 30, 2005).
Bourdon V et al., "Introns and their positions affect the transation activity of mRNA in plant cells", *EMBO Reports*, vol. 2, No.5 pp. 394-398 (2001).
International Search Report in corresponding International Application PCT/US05/35854, dated Feb. 19, 2009.
DD149398, "Bispecific antibody having the ability of substitution for functional protein", EMBL Record dated Nov. 9, 2005, (EMBL [online] Hinxton, Cambridge, UK), EMBL Nucleotide Sequence Submissions, retrieved from EBI accession No. EMBL:DD149398, Database accession No. DD149398.
ACC47228, "Hu266 N56T heavy chain encoding DNA", Geneseq Record dated Aug. 18, 2003, (Geneseq [online] New York, NY, US), Science Geneseq, retrieved from EBI accession No. GSN:ACC47228, Database accession No. ACC47228.

* cited by examiner

*Primary Examiner*—Larry R. Helms
*Assistant Examiner*—Meera Natarajan
(74) *Attorney, Agent, or Firm*—Lando & Anastasi, LLP

(57) ABSTRACT

Nucleic acid molecules modified to enhance recombinant protein, e.g., antibody, expression and/or reduce or eliminate mis-spliced and/or intron read-through (IRT) by-products are disclosed. The invention also provides methods for producing proteins devoid of mis-spliced and/or intron read-through by-products by the use of such vectors in host cells under cell culture conditions suitable for recombinant protein expression.

38 Claims, 11 Drawing Sheets

```
  1 GTGAGTCCTG TCGACTCTAG AGCTTTCTGG GGCAGGCCAG GCCTGACTTT GGCTGGGGGC
 61 AGGGAGGGGG CTAAGGTGAC GCAGGTGGCG CCAGCCAGGC GCACACCCAA TGCCCATGAG
121 CCCAGACACT GGACGCTGAA CCTCGCGGAC AGTTAAGAAC CAGGGGCCT CTGCGCCCTG
181 GGCCCAGCTC TGTCCCACAC CGCGGTCACA TGCACCACC TCTCTTGCAG CCTCCACCAA
                                                                A   S   T   K
241 GGGCCCATCG GTCTTCCCCC TGGCACCCTC CTCCAAGAGC ACCTCTGGGG GCACAGCGGC
      G   P   S     V   F   P     L   A   P     S   K   S     T   S   G     G   T   A   A
301 CCTGGGCTGC CTGGTCAAGG ACTACTTCCC CGAACCGGTG ACGGTGTCGT GGAACTCAGG
      L   G   C     L   V   K     D   Y   F   P     E   P   V     T   V   S     W   N   S   G
361 CGCCCTGACC AGCGGCGTGC ACACCTTCCC GGCTGTCCTA CAGTCCTCAG GACTCTACTC
      A   L   T     S   G   V     H   T   F   P     A   V   L     Q   S   S     G   L   Y   S
421 CCTCAGCAGC GTGGTGACCG TGCCCTCCAG CAGCTTGGGC ACCCAGACCT ACATCTGCAA
      L   S   S     V   V   T     V   P   S   S     S   L   G     T   Q   T     Y   I   C   N
481 CGTGAATCAC AAGCCCAGCA ACACCAAGGT GGACAAGAAA GTTGGTGAGA GGCCAGCACA
      V   N   H     K   P   S     N   T   K   V     D   K   K     V
541 GGGAGGGAGG GTGTCTGCTG GAAGCCAGGC TCAGCGCTCC TGCCTGGACG CATCCCGGCT
601 ATGCAGTCCC AGTCCAGGGC AGCAAGGCAG GCCCCGTCTG CCTCTTCACC CGGAGGCCTC
661 TGCCCGCCCC ACTCATGCTC AGGGAGAGGG TCTTCTGGCT TTTTCCCCAG GCTCTGGGCA
721 GGCACAGGCT AGGTGCCCCT AACCCAGGCC CTGCACACAA AGGGGCAGGT GCTGGGCTCA
781 GACCTGCCAA GAGCCATATC CGGGAGGACC CTGCCCCTGA CCTAAGCCCA CCCCAAAGGC
841 CAAACTCTCC ACTCCCTCAG CTCGGACACC TTCTCTCCTC CCAGATTCCA GTAACTCCCA
901 ATCTTCTCTC TGCAGAGCCC AAATCTTGTG ACAAAACTCA CACATGCCCA CCGTGCCCAG
                             E   P     K   S   C     D   K   T   H     T   C   P     P   C   P
961 GTAAGCCAGC CCAGGCCTCG CCCTCCAGCT CAAGGCGGGA CAGGTGCCCT AGAGTAGCCT
1021 GCATCCAGGG ACAGGCCCCA GCCGGGTGCT GACACGTCCA CCTCCATCTC TTCCTCAGCA
                                                                                         A
1081 CCTGAACTCC TGGGGGGACC GTCAGTCTTC CTCTTCCCCC CAAAACCCAA GGACACCCTC
       P   E   L     L   G   G   P     S   V   F     L   F   P     P   K   P     K   D   T   L
1141 ATGATCTCCC GGACCCCTGA GGTCACATGC GTGGTGGTGG ACGTGAGCCA CGAAGACCCT
       M   I   S     R   T   P   E     V   T   C     V   V   V     D   V   S     H   E   D   P
1201 GAGGTCAAGT TCAACTGGTA CGTGGACGGC GTGGAGGTGC ATAATGCCAA GACAAAGCCG
       E   V   K     F   N   W   Y     V   D   G     V   E   V     H   N   A   K     T   K   P
1261 CGGGAGGAGC AGTACAACAG CACGTACCGT GTGGTCAGCG TCCTCACCGT CCTGCACCAG
       R   E   E     Q   Y   N   S     T   Y   R     V   V   S     V   L   T   V     L   H   Q
1321 GACTGGCTGA ATGGCAAGGA GTACAAGTGC AAGGTCTCCA ACAAAGCCCT CCCAGCCCCC
       D   W   L     N   G   K   E     Y   K   C     K   V   S     N   K   A   L     P   A   P
1381 ATCGAGAAAA CCATCTCCAA AGCCAAAGGT GGGACCCGTG GGGTGCGAGG GCCACATGGA
       I   E   K     T   I   S   K     A   K
1441 CAGAGGCCGG CTCGGCCCAC CCTCTGCCCT GAGAGTGACC GCTGTACCAA CCTCTGTCCC
1501 TACAGGGCAG CCCCGAGAAC ACAGGTGTA CACCCTGCCC CCATCCCGGG AGGAGATGAC
              G   Q     P   R   E     P   Q   V   Y     T   L   P     S   R     E   E   M   T
1561 CAAGAACCAG GTCAGCCTGA CCTGCCTGGT CAAAGGCTTC TATCCCAGCG ACATCGCCGT
       K   N   Q     V   S   L     T   C   L     V   K   G   F     Y   P   S     D   I   A   V
1621 GGAGTGGGAG AGCAATGGGC AGCCGGAGAA CAACTACAAG ACCACGCCTC CCGTGCTGGA
       E   W   E     S   N   G     Q   P   E   N     N   Y   K     T   T   P     P   V   L   D
1681 CTCCGACGGC TCCTTCTTCC TCTATAGCAA GCTCACCGTG GACAAGAGCA GGTGGCAGCA
       S   D   G     S   F   F     L   Y   S   K     L   T   V     D   K   S     R   W   Q   Q
1741 GGGGAACGTC TTCTCATGCT CCGTGATGCA TGAGGCTCTG CACAACCACT ACACGCAGAA
       G   N   V     F   S   C     S   V   M   H     E   A   L     H   N   H     Y   T   Q   K
1801 GAGCCTCTCC CTGTCCCCGG GTAAATGA    (SEQ ID NO:1)
       S   L   S     L   S   P     G   K       (SEQ ID NO:2)
```

Figure 8

```
   1 GTGAGTCCTG TCGACTCTAG AGCTTTCTGG GGCAGGCCAG GCCTGACTTT GGCTGGGGGC
  61 AGGGAGGGGG CTAAGGTGAC GCAGGTGGCG CCAGCCAGGC GCACACCCAA TGCCCATGAG
 121 CCCAGACACT GGACGCTGAA CCTCGCGGAC AGTTAAGAAC CCAGGGGCCT CTGCGCCCTG
 181 GGCCCAGCTC TGTCCCACAC CGCGGTCACA TGGCACCACC TCTCTTGCAG CCTCCACCAA
                                                                A  S  T  K
 241 GGGCCCATCG GTCTTCCCCC TGGCGCCCTG CTCCAGGAGC ACCTCCGAGA GCACAGCGGC
      G  P  S   V  F  P    L  A  P  C  S  R  S   T  S  E    S  T  A  A
 301 CCTGGGCTGC CTGGTCAAGG ACTACTTCCC CGAACCGGTG ACGGTGTCGT GGAACTCAGG
      L  G  C   L  V  K    D  Y  F  P  E  P  V   T  V  S    W  N  S  G
 361 CGCCCTGACC AGCGGCGTGC ACACCTTCCC GGCTGTCCTA CAGTCCTCAG GACTCTACTC
      A  L  T   S  G  V    H  T  F  P  A  V  L   Q  S  S    G  L  Y  S
 421 CCTCAGCAGC GTGGTGACCG TGCCCTCCAG CAGCTTGGGC ACGAAGACCT ACACCTGCAA
      L  S  S   V  V  T    V  P  S  S  S  L  G   T  K  T    Y  T  C  N
 481 TGTAGATCAC AAGCCCAGCA ACACCAAGGT GGACAAGAGA GTTGGTGAGA GGCCAGCACA
      V  D  H   K  P  S    N  T  K  V  D  K  R   V
 541 GGGAGGGAGG GTGTCTGCTG GAAGCCAGGC TCAGCCCTCC TGCCTGGACG CACCCCGGCT
 601 GTGCAGCCCC AGCCCAGGGC AGCAAGGCAG GCCCCATCTG TCTCCTCACC TGGAGGCCTC
 661 TGACCACCCC ACTCATGCTC AGGGAGAGGG TCTTCTGGAT TTTTCCACCA GGCTCCGGGC
 721 AGCCACAGGC TGGATGCCCC TACCCCAGGC CCTGCGCATA CAGGGGCAGG TGCTGCGCTC
 781 AGACCTGCCA AGAGCCATAT CCGGGAGGAC CCTGCCCCTG ACCTAAGCCC ACCCCAAAGG
 841 CCAAACTCTC CACTCCCTCA GCTCAGACAC CTTCTCTCCT CCCAGATCTG AGTAACTCCC
 901 AATCTTCTCT CTGCAGAGTC CAAATATGGT CCCCCATGCC CACCATGCCC AGGTAAGCCA
                         E  S       K  Y  G      P  P  C    P  P  C  P
 961 ACCCAGGCCT CGCCCTCCAG CTCAAGGCGG GACAGGTGCC CTAGAGTAGC CTGCATCCAG
1021 GGACAGGCCC CAGCCGGGTG CTGACGCATC CACCTCCATC TCTTCCTCAG CACCTGAGTT
                                                               A  P  E  F
1081 CCTGGGGGGA CCATCAGTCT TCCTGTTCCC CCCAAAACCC AAGGACACTC TCATGATCTC
      L  G  G   P  S  V    F  L  F  P  P  K  P   K  D  T    L  M  I  S
1141 CCGGACCCCT GAGGTCACGT GCGTGGTGGT GGACGTGAGC CAGGAAGACC CCGAGGTCCA
      R  T  P   E  V  T    C  V  V  V  D  V  S   Q  E  D    P  E  V  Q
1201 GTTCAACTGG TACGTGGATG GCGTGGAGGT GCATAATGCC AAGACAAAGC CGCGGGAGGA
      F  N  W   Y  V  D    G  V  E  V  H  N  A   K  T  K    P  R  E  E
1261 GCAGTTCAAC AGCACGTACC GTGTGGTCAG CGTCCTCACC GTCCTGCACC AGGACTGGCT
      Q  F  N   S  T  Y    R  V  V  S  V  L  T   V  L  H    Q  D  W  L
1321 GAACGGCAAG GAGTACAAGT GCAAGGTCTC CAACAAAGGC CTCCCGTCCT CCATCGAGAA
      N  G  K   E  Y  K    C  K  V  S  N  K  G   L  P  S    S  I  E  K
1381 AACCATCTCC AAAGCCAAAG GTGGGACCCA CGGGGTGCGA GGGCCACATG GACAGAGGTC
      T  I  S   K  A  K
1441 AGCTCGGCCC ACCCTCTGCC CTGGGAGTGA CCGCTGTGCC AACCTCTGTC CCTACAGGGC
                                                                         G
1501 AGCCCCGAGA GCCACAGGTG TACACCCTGC CCCCATCCCA GGAGGAGATG ACCAAGAACC
      Q  P  R  E   P  Q  V   Y  T  L   P  P  S  Q  E  E  M   T  K  N
1561 AGGTCAGCCT GACCTGCCTG GTCAAAGGCT TCTACCCCAG CGACATCGCC GTGGAGTGGG
      Q  V  S  L   T  C  L   V  K  G   F  Y  P  S   D  I  A   V  E  W
1621 AGAGCAATGG GCAGCCGGAG AACAACTACA AGACCACGCC TCCCGTGCTG GACTCCGACG
      E  S  N  G   Q  P  E   N  N  Y   K  T  T  P   V  L  D   S  D
1681 GCTCCTTCTT CCTCTACAGC AGGCTAACCG TGGACAAGAG CAGGTGGCAG GAGGGGAATG
      G  S  F  F   L  Y  S   R  L  T   V  D  K  S   R  W  Q   E  G  N
1741 TCTTCTCATG CTCCGTGATG CATGAGGCTC TGCACAACCA CTACACACAG AAGAGCCTCT
      V  F  S  C   S  V  M   H  E  A   L  H  N  H   Y  T  Q   K  S  L
1801 CCCTGTCTCT GGGTAAATGA (SEQ ID NO:3)
      S  L  S  L   G  K    (SEQ ID NO:4)
```

Figure 9

```
GTGAGTCCTGTGTCGACTCTAGAGCTTTCTGGGGCAGGCCAGGCCTGACTTTGGCTGGGGCAGGGAGGGGCT
AAGGTGACGCAGTGGCGCCAGCCAGGCCCAATGCCCAGACACTGGACGCTGAACCTC
GCGGACAGTTAAGAACCCAGGGGCCTCTGCGCCCTGGGCCCAGCTCTGTCCCACACCGGTCACATGGCAC
CACCTCTCTTGCAGCCCTCCACCAAGGCCCATCGGTCTTCCCCCTGGCCACCCTCTGG
GGGCACAGCGGCCCTGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACGTGAATCACAAGCCCAGCAACAC
CAAGGTGGACAAGAAAGTTGGTGAGAGGCCAGCAGGGAGGGTGTCTGCTGGGAAGCCAGGCTCAGCG
CTCCTGCCTGACGCCATCCCGGCTATGCAGTCCCAGTCCAGGGCAGCAAGGCAGGCCCCGTCTGCCTCTTCA
CCCGGAGGCCTCTGTGCCCGCCCCACTCATGCTCAGGGAGGAGGGTCTTCTGGCTTTTTCCCCAGGCTCTGGGCA
GGCACAGGCTAGGTGCCCCTAACCCAGGCCTGGGCTCCTGACCCAAAGGCCAGTGCTGGGCTCAGACCTGCCAAGA
GCCATATCCGGGAGGACCCTGCCCCTGACCTAAGCTCCCAAATCTTCTCCACTCCCTCAGCTCG
GACACCTTCTCCTCCCAGATTCCAGTAACTCCCAGCCCTGCCCAGTAAGCCCAGCCCCTCCAGCCCTCAGCTCCCAAATCTTGTGACAAAA
CTCACACATGCCCACCGTGCATCCAGGGACACAGGCCCCAGCAGCCTGCTGACACGTCCACCTCCATCTCTTCCTCAGCA
CTAGAGTAGCCTGCATCCAGGGACACAGGCCCCAGCAGCCTGCTGACACGTCCCCAAAACCAAGGACACCCCTGAGTTCAACTGGTACGTG
CCTGAACTCCTGGGGGACCGTCAGTCTTGGTGGTGAGCGTGGACGTGAGCCACGAAGACCCTGAGGTCAAGTTCAACTGGTACGTG
ACCCCTGAGGTCACATGCGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCTCCCGTGCTGGAC
TCCGACGGCTCCTTCTTCCTCTATAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCCCCGGGTAAA
TGA (SEQ ID NO:5)
```

Figure 10

GTGAGTCCTGTCGACTCTAGAGCTTTCTGGGCAGGCCTGACTTTGGCTGTGGGCAGGGAGGGGCTAA
GGTGACGCAGGTGGCGCAGCCAGGCGCACACCCAGGCCCATGCCCAGACACTGGACGCTGAACCTCGCGG
ACAGTTAAGAACCCAGAGGGCCCTGCGCGCCCAGCTCTGTCCCACACCGGGTCACATGGCACCACCTC
TCTTGCAGCCTCCACCAAGGCCCATCGGTCTTCCCCGCCCTGCTCCAGGAGCACCTCCGAGAGCACAG
CGGCCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGTGCC
CTCCAGCAGCTTGGGCACGAAGACCTACACCTGCAATGTAGATCACAAGCCCAGCAACACCAAGGTGGACAAGA
GAGTTGAGTCCAAATATGGTCCCCCAGCACCTGAGTTCCTGGGGGACCATCAGTCTTC
CTGTTCCCCCCAAAACCCAAGGACACACTCTCATGATCTCCCGGACCCCTGAGGTCACGTGCGTGGTGGACGT
GAGCCAGGAAGACCCCGAGGTCCAGTTCAACTGGTACGTGGATGGCGTGGAGGTGCATAATGCCAAGACAAAGC
CGCGGGAGGAGCAGTTCAACAGCACGTACCGTGTGGTCAGCGTCCTCACCGTCCTGCACCAGGACTGGCTGAAC
GGCAAGGAGTACAAGTGCAAGGTCTCCAACAAAGGCCCTCCCCGTCCCCCATCGAGAAAACCATCTCCAAAGCCAA
AGGGCAGCCCCGAGAGCCACAGGTGTACACCCTGCCCCCATCCCAGGAGGAGATGACCAAGAACCAGGTCAGCC
TGACCTGCCTGGTCAAAGGCTTCTACCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAGGCTAACCGTGGACAA
GAGCAGGTGGCAGGAGGGGAATGTCTTCTCATGCTCCGTGATGCATGAGGCTCTGCACAACCACTACACACAGA
AGAGCCTCTCCCTGTCTCTGGGTAAATGA (SEQ ID NO: 6)

Figure 11

METHODS AND COMPOSITIONS FOR IMPROVING RECOMBINANT PROTEIN PRODUCTION

CROSS-REFERENCE TO RELATED APPLICATION

This application claims priority to U.S. Patent Application Serial No. 60/616,474, filed on Oct. 5, 2004, the entire contents of which are hereby incorporated by reference.

BACKGROUND OF THE INVENTION

Expression vectors for the production of recombinant proteins have existed since at least the mid 1980s. Typically, vector-based strategies for recombinant protein expression have largely been employed in basic research and for small-scale experimentation where the absolute purity of a protein preparation is not critical. In contrast, when recombinant proteins are used for therapeutic applications, even minor contaminants, for example, the presence of mis-spliced or intron read-through by-products can diminish the activity and yield of the resultant therapeutic proteins. Administration of therapeutic proteins having mis-spliced or read-through protein sequences to patients may increase the possibility of undesirable side effects.

Such by-products are also troublesome for manufacturing. The presence of by-products can compromise the purification process because such by-products are typically similar to the desired proteins in terms of size, affinity, or bioactivity. Still further, it has been observed that scaling up protein expression using recombinant host cells typically results in increasing amounts of by-products as compared to the desired product, particularly if the cells are cultured under less than optimal cell culture conditions. Such sub-optimal cell culture conditions frequently occur in large scale protein production, for example, at the end of a biofermenter run or when, for other reasons, where the health of the large scale culture deteriorates.

Accordingly, there exists a need for methods for improving recombinant protein production, particularly, for the large-scale production of therapeutic proteins.

SUMMARY OF THE INVENTION

The present invention provides methods and compositions for improving recombinant protein or peptide expression and/or production. In one embodiment, nucleic acid molecules are provided that are modified to reduce or eliminate mis-spliced and/or intron read-through by-products, and/or to enhance recombinant protein expression. In certain embodiments, the nucleic acids encode recombinant antibodies (also referred to herein as immunoglobulins), or fragments thereof. The invention further includes vectors (e.g., expression vectors) modified to reduce or eliminate mis-spliced and/or intron read-through by-products and/or to enhance recombinant protein expression; host cells, e.g., mammalian host cells, including such nucleic acid molecules and vectors; and methods for culturing such cells to produce the recombinant proteins or peptides, e.g., in large-scale. Compositions, e.g., pharmaceutical compositions, of recombinant proteins or peptides, e.g., antibodies, substantially free of mis-spliced and/or intron read-through products, are also disclosed. These compositions are suitable for therapeutic use, including, for example, the treatment of neurodegenerative and malignant disorders.

Accordingly, in one aspect, the invention features a nucleic acid molecule (e.g., a modified or recombinant nucleic acid molecule) that includes a nucleotide sequence having one or more intron and exon sequences, wherein at least one intron sequence has been modified (e.g., deleted) compared to the naturally-occurring sequence. In one embodiment, the modified nucleic acid enhances protein expression, e.g., yields a protein expression at least two fold higher than the naturally-occurring sequence in a stable cell line (e.g., a CHO cell line). In another embodiment, the modified nucleic acid reduces or eliminates mis-spliced or intron read-through (IRT) by-product(s). In one embodiment, the nucleic acid molecule directs enhanced expression and/or reduces or eliminates intron read-through (IRT) by-product(s) of a desired protein or peptide, for example, an antibody or a fragment thereof (e.g., an immunoglobulin heavy chain) relative to a naturally occurring sequence (e.g., a genomic sequence). The protein or peptide can be of mammalian origin, e.g., human or murine, typically, of human origin. The nucleic acid molecule described herein is understood to refer to a modified form from the naturally-occurring sequence. In some embodiments, the nucleic acid molecule is isolated or purified. In other embodiments, it is a recombinant molecule.

In one embodiment, the nucleic acid molecule has at least one, two, three introns, or up to all but one intron, deleted compared to the naturally-occurring sequence (e.g., the genomic sequence). For example, an intron that facilitates intron read-through (IRT) can be deleted from the naturally-occurring sequence. In other embodiments, the nucleic acid molecule is modified by one or more of: re-arranging the intron/exon configuration (e.g., intron/exon 5' to 3' order); deleting a portion of one or more introns; or replacing an intron or portion thereof with a heterologous intron sequence, such that enhanced protein expression and/or reduction or elimination of mis-spliced or intron read-through (IRT) by-product(s) occurs.

In a related embodiment, the nucleic acid molecule includes a nucleotide sequence (e.g., a human genomic sequence) encoding an antibody heavy chain or a fragment thereof. For example, the nucleotide sequence can include one or more nucleotide (e.g., exon) sequences encoding a heavy chain variable region, a hinge region, and a first, second, and third constant regions (e.g., $C_H1$, $C_H2$, $C_H3$) of an immunoglobulin subtype, e.g., an immunoglobulin G subtype (e.g., an IgG1, IgG2, IgG3, or IgG4 antibody subtype). Typically, the immunoglobulin subtype is from mammalian origin, e.g., murine or human. In one embodiment, a human IgG1 or IgG4, or a mutated version thereof is chosen. For example, the constant region of an immunoglobulin can be mutated to result in one or more of: increased stability, reduced effector function, or reduced complement fixation. In one embodiment, human IgG4 is mutated to increase stability, e.g., having a replacement at residue 241 from serine to proline to increase stability of the hinge region. In other embodiments, the constant region is mutated to reduce glycosylation.

In one embodiment, the nucleic acid molecule is modified to delete at least one intron that facilitates intron-read through of the sequence. For example, an intron between $C_H2$ and $C_H3$ of the immunoglobulin heavy chain constant region can be deleted. Examples of other heavy chain immunoglobulin introns that can be deleted individually or in combination include an intron between the heavy chain variable region and $C_H1$, an intron between $C_H1$ and the hinge region, and an intron between the hinge region and $C_H2$, of the immunoglobulin heavy chain constant region. Any combination of the preceding introns can be deleted, including a combination of two, three introns, or up to all but one intron, of the aforesaid introns. In some embodiments, three introns of the heavy chain constant region are deleted, for example, the intron between $C_H1$ and the hinge region, the intron between the hinge region and $C_H2$, and the intron between $C_H2$ and $C_H3$. The following exemplary combinations of intron deletions of a heavy chain immunoglobulin are also within the scope of the present invention: an intron between $C_H1$ and the hinge region, and an intron between $C_H2$ and $C_H3$; an intron between $C_H1$ and the hinge region, and an intron between the hinge region and $C_H2$; an intron between the hinge region and $C_H2$ and an intron between $C_H2$ and $C_H3$ of the immunoglobulin heavy chain constant region.

In some embodiments, the nucleic acid molecule includes a nucleotide sequence represented by the formula:

$V_H$-Int1-$C_H$1-Int2-Hinge-Int3-$C_H$2-Int4-$C_H$3, wherein $V_H$ is a nucleotide sequence encoding a heavy chain variable region;

$C_H1$, $C_H2$, and $C_H3$ are nucleotide sequences encoding the corresponding heavy chain constant region, e.g., a naturally-occurring or a mutated form of human IgG1 or IgG4 heavy chain gene;

Hinge is a nucleotide sequence encoding a hinge region of a heavy chain constant region, e.g., a naturally-occurring or a mutated form of human IgG1 or IgG4 heavy chain gene; and Int1, Int2, Int3 and Int4 are introns from the heavy chain genomic sequence. In one embodiment, the intron between $C_H2$ and $C_H3$, represented herein as Int4 is deleted. In other embodiments, one, two, or typically three of the introns between $C_H1$ and the hinge region, between the hinge region and $C_H2$, and/or between $C_H2$ and $C_H3$, represented herein as Int2, Int3 and Int4, are deleted. Additional schematic representations of the intron/exon arrangements of the heavy chain genomic sequence are shown in FIGS. 1, 5, and 7.

Typically, at least one intron is present in the nucleic acid molecule, for example, the intron between the heavy chain variable region and $C_H1$, represented herein as Int1. Examples of other heavy chain immunoglobulin introns that can be present individually or in combination include an intron between $C_H1$ and the hinge region; an intron between the hinge region and $C_H2$; and an intron between $C_H2$ and $C_H3$ of the immunoglobulin heavy chain constant region. It is often desirable to include at least one intron in the modified nucleic acid molecule. Without being bound by theory, introns are believed to influence a number of events in the protein production process, including transcription rate, polyadenylation, mRNA export, translational efficiency, and mRNA decay.

In one embodiment, the nucleic acid molecule includes a nucleotide sequence represented by the formula:

$V_H$-Int1-$C_H$1-Int2-Hinge-Int3-$C_H$2-$C_H$3, wherein $V_H$ is a nucleotide sequence encoding a heavy chain variable region;

$C_H1$, $C_H2$, and $C_H3$ are nucleotide sequences encoding the corresponding heavy chain constant region, e.g., a naturally-occurring or mutated form of human IgG1 or IgG4 heavy chain gene;

Hinge is a nucleotide sequence encoding a hinge region of a heavy chain constant region, e.g., a naturally-occurring or mutated form of human IgG1 or IgG4 heavy chain gene; and Int1, Int2 and Int3 are introns from the heavy chain genomic sequence. In one embodiment, the nucleotide sequence consists essentially of the constituents depicted above, e.g., without an intervening sequence that alters the structure or function.

In other embodiments, the nucleic acid molecule includes a nucleotide sequence represented by the formula:

$V_H$-Int1-$C_H$1-Hinge-$C_H$2-$C_H$3, wherein $V_H$ is a nucleotide sequence encoding a heavy chain variable region;

$C_H1$, $C_H2$, and $C_H3$ are nucleotide sequences encoding the corresponding heavy chain constant region, e.g., a naturally-occurring or mutated form of human IgG1 or IgG4 heavy chain gene;

Hinge is a nucleotide sequence encoding a hinge region of a heavy chain constant region, e.g., a naturally-occurring or mutated form of human IgG1 or IgG4 heavy chain gene; and Int1 is an intron from the heavy chain genomic sequence. In one embodiment, the nucleotide sequence consists essentially of the constituents depicted above, e.g., without an intervening sequence that alters the structure or function.

The genomic nucleotide and corresponding amino acid sequences for human IgG1 are shown in FIG. 8 (SEQ ID NO: 1 and 2, respectively). Exons encoding $C_H1$, the hinge region, $C_H2$, and $C_H3$ are located at about nucleotides 231 to 524, 916 to 960, 1079 to 1408, and 1506 to 1829, of FIG. 8 (SEQ ID NO:1), respectively. The Int1, Int2, Int3 and Int4 correspond to introns from the human IgG1 heavy chain genomic sequence located from about nucleotides 1 to 230, about nucleotides 525 to 915, about nucleotides 961 to 1078, and about nucleotides 1409 to 1505, of FIG. 8 (SEQ ID NO:1), respectively.

The genomic nucleotide and corresponding amino acid sequences for mutated human IgG4 are shown in FIG. 9 (SEQ ID NO:3 and 4 respectively). Exons encoding $C_H1$, the hinge region, $C_H^2$, and $C_H3$ are located at about nucleotides 231 to 524, 916 to 952, 1071 to 1400, and 1498 to 1820, of FIG. 9 (SEQ ID NO:3), respectively. Int1, Int2, Int3, and Int4 correspond to introns from the human IgG4 heavy chain genomic sequence located from about nucleotides 1 to 230, about nucleotides 525 to 916, about nucleotides 953 to 1070, and about nucleotides 1401 to 1497, of FIG. 9 (SEQ ID NO:3), respectively.

Examples of modified nucleic acid molecules of the present invention include a human genomic heavy chain constant region sequence having a deletion of the intron between CH2 and CH3 of, human IgG1, corresponding to about nucleotides 1409 to 1505 of FIG. 8 (SEQ ID NO:1), or of mutated human IgG4, corresponding to about nucleotides 1401 to 1497 of FIG. 9 (SEQ ID NO:3). Examples of other heavy chain immunoglobulin introns that can be deleted individually or in combination include an intron between the heavy chain variable region and CH1 of, human IgG1, corresponding to about nucleotides 1 to 230 of FIG. 8 (SEQ ID NO:1), or mutated human IgG4, corresponding to about nucleotides 1 to 230 of FIG. 9 (SEQ ID NO:3); an intron between CH1 and the hinge region of, human IgG1, corresponding to about nucleotides 525 to 915 of FIG. 8 (SEQ ID NO:1), or mutated human IgG4, corresponding to about nucleotides 525 to 916 of FIG. 9 (SEQ ID NO:3); and an intron between the hinge region and CH2, of human IgG1, corresponding to about nucleotides 961 to 1078 of FIG. 8 (SEQ ID NO:1), or mutated human IgG4, corresponding to about nucleotides 953 to 1070 of FIG. 9 (SEQ ID NO:3). Any combination of the preceding introns can be deleted, including a combination of two, three, four introns, or up to all but one intron, of the aforesaid introns can be deleted. In some embodiments, three introns of the heavy chain constant region are deleted, for example, the intron between CH1 and the hinge region, between the hinge region and CH2, and between CH2 and CH3. In some embodiments, the nucleic acid molecule includes one or more of the exonic nucleotide sequences, and one or more (but not all) of the intronic nucleotide sequences, for human IgG1 or IgG4 disclosed herein, or a sequence substantially identical thereto. In a related embodiment, the nucleic acid molecule has a deletion in one or more (but not all) of the intronic nucleotide sequences, for human IgG1 or IgG4 disclosed herein, or a sequence substantially identical thereto.

In one embodiment, the modified nucleic acid molecule includes the nucleotide sequence encoding human IgG1 shown as FIG. 10 (SEQ ID NO:5) or a sequence substantially identical thereto (e.g., a sequence at least 85%, 90%, 95%, or 99% identical to SEQ ID NO:5, or having one, five, ten, fifty or more nucleotide changes compared to the nucleotide sequence of SEQ ID NO:5).

In another embodiment, the modified nucleic acid molecule includes the nucleotide sequence of modified human IgG4 shown as FIG. 11 (SEQ ID NO:6) or a sequence substantially identical thereto (e.g., a sequence at least 85%, 90%, 95%, or 99% identical to SEQ ID NO:6, or having one, five, ten, fifty or more nucleotide changes compared to the nucleotide sequence of SEQ ID NO:6).

The modified nucleic acid molecule can include a nucleotide sequences encoding a light and heavy chain antibody or immunoglobulin sequence. Such sequences can be present in the same nucleic acid molecule (e.g., the same expression vector) or alternatively, can be expressed from separate nucleic acid molecules (e.g., separate expression vectors). Typically, the encoded antibody or immunoglobulins or fragments thereof can include at least one, and preferably two full-length heavy chains, and at least one, and preferably two light chains. Alternatively, the encoded immunoglobulins or fragments thereof can include only an antigen-binding fragment (e.g., an Fab, F(ab')$_2$, Fv or a single chain Fv fragment). The antibody or fragment thereof can be a monoclonal or single specificity antibody. The antibody or fragment thereof can also be a human, humanized, chimeric, CDR-grafted, or in vitro generated antibody. In yet other embodiments, the antibody has a heavy chain constant region chosen from, e.g., IgG1, IgG2, IgG3, IgG4, IgM, IgA1, IgA2, IgD, and IgE; more particularly, chosen from, e.g., IgG1, IgG2, IgG3, and IgG4. In another embodiment, the antibody has a light chain chosen from, e.g., kappa or lambda.

In another embodiment, the nucleic acid molecule includes a variable region, for example a humanized, chimeric, CDR-grafted, or in vitro generated variable region. Typically, the variable region specifically binds to a predetermined antigen, e.g., an antigen associated with a disorder, e.g., a neurodegenerative or a malignant disorder.

In one embodiment, the disorder is a neurodegenerative disorder and the antibody binds to an amyloid protein, for example, an Aβ peptide (e.g., a human Aβ peptide). For example, the antibody can be a humanized antibody against an Aβ peptide having a heavy chain and light chain variable regions containing one or more complementarity determining regions (CDRs) from a murine antibody, e.g., the mouse anti-Aβ 3D6 antibody. The variable region of the humanized antibody typically includes a human or substantially human framework region. In one embodiment, the nucleic acid molecule includes the heavy and light chain variable regions of the humanized anti-Aβ peptide antibody.

In another embodiment, the disorder is a malignant or cancerous disorder and the antibody binds to a cell surface protein associated with malignant cells (e.g., a solid tumor cell) for example a 5T4 protein. 5T4 protein is a 72 kDa glycoprotein expressed widely in carcinomas, particularly colorectal and gastric metastatic cancers. In some embodiments, the antibody is a humanized antibody against a 5T4 protein having a heavy chain and light chain variable regions containing one or more complementarity determining regions (CDRs) from a murine antibody. In one embodiment, the nucleic acid molecule includes the heavy and light chain variable regions of the humanized anti-5T4 antibody.

In another aspect, the invention features a vector (e.g., an expression vector) including one or more of the foregoing modified nucleic acid molecules. The vector can additionally include a nucleotide sequence that enhances one or more of: replication, selection, mRNA transcription, mRNA stability, protein expression or protein secretion, in a host cell. For example, the vector may include nucleotide sequences responsible for replication or enhancer expression, enhancer promoter elements, nucleotide sequences encoding a leader sequence, a gene encoding a selectable marker (e.g., DHFR), an internal ribosomal entry site sequence (IRES), and polyadenylation sequences).

In another aspect, the invention provides a cell, for example, a eukaryotic host cell, e.g., a mammalian host cell (e.g., a Chinese Hamster Ovary (CHO) cell), including one of the foregoing nucleic acid molecules and/or vectors, e.g., expression vectors. The cell can be transiently or stably transfected with the nucleic acid sequences of the invention.

In another aspect, the invention provides a method for enhancing expression of recombinant proteins or peptides, e.g., antibodies, or expressing recombinant proteins or peptides, e.g., antibodies having reduced levels of (e.g., substantially free of) mis-spliced and/or intron read-through products, compared to a reference, e.g., a naturally occurring genomic sequence. The method includes introducing a nucleic acid molecule as described herein into a host cell, e.g., a mammalian host cell (e.g., a CHO cell); culturing said host cell under conditions that allow expression of the recombinant protein or peptide to produce a culture of host cells; and optionally, obtaining, e.g., purifying, the recombinant protein or peptide, from the culture of host cells (e.g., host cell supernatants).

The method can further include the steps of identifying (e.g., detecting and/or determining the level of) IRT or an IRT product, in a nucleic acid sample, e.g., an mRNA sample from the host cell, by contacting said sample with nucleic acid probes complementary to an intron and an adjacent exon sequence, or alternatively, complementary to adjacent exon sequences, under conditions that allow hybridization of the nucleic acid sample and the probes; detecting the resulting complex, e.g., by PCR amplification of the probe sequences. Detection of a complex, e.g., a PCR amplified product, in the sample containing the nucleic acid probe complementary to the intron sequence is indicative of the occurrence IRT or the IRT product. The level of an IRT product can be quantified as described, e.g., in Example 1.

In another aspect, a method for producing an antibody or fragment thereof having reduced (e.g., substantially devoid of) intron read-through (IRT) heavy chain by-product, compared to a standard reference, e.g., a naturally occurring genomic sequence, is provided. The method includes culturing a cell, e.g., a mammalian cell (e.g., a CHO cell) containing a nucleic acid molecule as described herein and, optionally, a nucleic acid encoding an antibody light chain, under conditions such that the heavy and light chains are expressed and, optionally, operatively associate. The antibody or fragment thereof are, optionally, purified from the cell culture. Typically, the antibody, or fragment thereof, has reduced mis-spliced or intron read-through (IRT) heavy chain by-product.

The method can further include the steps of detecting and/or determining the level of IRT, or an IRT product, in a sample, e.g., an mRNA sample from the host cell; contacting said sample with nucleic acid probes complementary to an intron and an adjacent exon sequence, or alternatively, complementary to adjacent exon sequences, under conditions that allow hybridization of the nucleic acid sample and the probes; detecting the resulting complex, e.g., by PCR amplification of the probe sequences. Detection of a complex, e.g., a PCR amplified product, in the sample containing the nucleic acid probe complementary to the intron sequence is indicative of the occurrence IRT, or the IRT product. The level of an IRT product can be quantified as described, e.g., in Example 1.

In another aspect, the invention provides a method of reducing intron read-through (IRT) antibody heavy chain byproduct expressed from a genomic heavy chain sequence, by deleting at least one intron from said sequence, wherein said intron facilitates IRT.

In another aspect, the invention features a method of identifying (e.g., detecting and/or determining the level of) IRT or an IRT product, in a sample, e.g., a nucleic acid sample. The method includes: obtaining a nucleic acid sample, e.g., an mRNA sample from a cell, e.g., a recombinant cell (e.g., a host cell as described herein); contacting said nucleic acid sample with nucleic acid probes complementary to an intron and an adjacent exon sequence, or alternatively, complementary to adjacent exon sequences, under conditions that allow hybridization of the nucleic acid sample and the probes; detecting the resulting complex, e.g., by PCR amplification of the probe sequences. Detection of a complex, e.g., a PCR amplified product, in the sample containing the nucleic acid probe complementary to the intron sequence is indicative of the occurrence IRT, or the IRT product. The level of an IRT product can be quantified as described, e.g., in Example 1.

In another aspect, the invention features an antibody (e.g., a recombinant antibody), or fragment thereof, having reduced (e.g., substantially free of) mis-spliced and/or intron readthrough products, compared to a reference, e.g., a naturally occurring genomic sequence, produced according to the methods disclosed herein. In one embodiment, the antibody or fragment thereof is a chimeric, humanized, CDR-grafted or an in vitro generated antibody. Typically, the antibody or fragment thereof has a variable region that specifically binds to a predetermined antigen, e.g., an antigen associated with a disorder, e.g., a neurodegenerative or a malignant disorder.

In another aspect, the invention provides a composition, e.g., a pharmaceutical composition, containing recombinant proteins or peptides, e.g., antibodies, having reduced (e.g., substantially free of) mis-spliced and/or intron read-through products, compared to a reference, e.g., a naturally occurring genomic sequence, and a pharmaceutically acceptable carrier. These compositions are suitable for therapeutic use, including, for example, treatment of neurodegenerative and malignant disorders.

Other features and advantages of the invention will be apparent from the following detailed description and claims.

BRIEF DESCRIPTION OF THE DRAWINGS

FIG. 8 shows the genomic nucleotide and corresponding amino acid sequences for human IgG1 are shown in (SEQ ID NO: 1 and 2, respectively). Exons encoding $C_H1$, the hinge region, $C_H2$, and $C_H3$ are located at about nucleotides 231 to 524, 916 to 960, 1079 to 1408, and 1506 to 1829, respectively (SEQ ID NO:1). The Int1, Int2, Int3 and Int4 correspond to introns from the human IgG1 heavy chain genomic sequence located from about nucleotides 1 to 230, about nucleotides 525 to 915, about nucleotides 961 to 1078, and about nucleotides 1409 to 1505, respectively (SEQ ID NO:1).

FIG. 9 shows the genomic nucleotide and corresponding amino acid sequences for human IgG4 are shown in (SEQ ID NO:3 and 4, respectively). Exons encoding $C_H1$, the hinge region, $C_H2$, and $C_H3$ are located at about nucleotides 231 to 524, 916 to 952, 1071 to 1400, and 1498 to 1820, respectively, (SEQ ID NO:3). Int1, Int2, Int3, and Int4 correspond to introns from the human IgG4 heavy chain genomic sequence located from about nucleotides 1 to 230, about nucleotides 525 to 916, about nucleotides 953 to 1070, and about nucleotides 1401 to 1497, respectively (SEQ ID NO:3).

FIG. 10 shows the genomic nucleotide sequence of human IgG1 (SEQ ID NO:5) having the intron between $C_H2$ and $C_H3$ of the constant region deleted.

FIG. 11 shows the genomic nucleotide sequence of modified human IgG4 (SEQ ID NO:6) having the following intron deletions: intron between CH1 and hinge, intron between hinge and $C_H2$, and intron between $C_H2$ and $C_H3$.

DETAILED DESCRIPTION OF THE INVENTION

Figure 1:
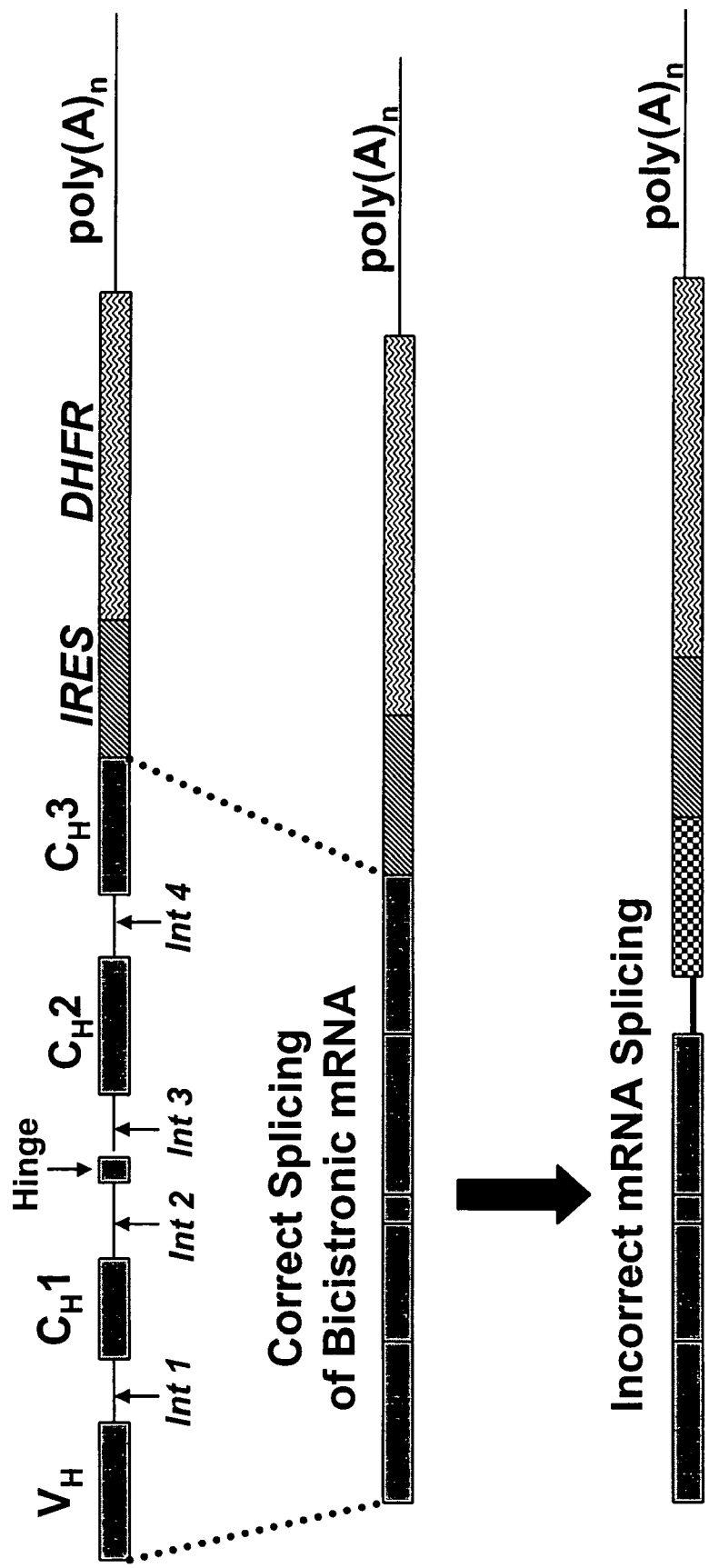
FIG. 1 depicts the expected pre-mRNA transcribed from the expression vector containing the 3D6 IgG gene (top) as well as the correctly spliced mRNA (middle) and intron-read through mRNA (bottom).

A number of approaches may be taken in the design and construction of expression vectors, and the process typically requires substantial trial and error experimentation before reasonable levels of a protein are produced. A significant consideration in the design process concerns the use of intron sequences in the construction of the vector. In one approach, an entire gene sequence may be utilized as it occurs naturally—containing the full complement of both intronic and exonic sequences. In such a case, it is expected that post-transcriptional splicing machinery within the cell will excise intronic sequences to yield a mature mRNA containing only exonic sequences of the gene. A second approach is to utilize sequence corresponding to the cDNA of the gene only. In this case, it is predicted that no splicing events occur and the pre-mRNA sequence is substantially the same as the mRNA sequence in protein coding content. In yet a third case, vector construction involves the selection and placement of introns not normally associated with the original gene sequence.

The effect of intronic sequences on the expression of genes within the context of a vector is incompletely understood. It has been reported that introns may effect a number of events in the process of protein production including transcription rate, polyadenylation, mRNA export, translational efficiency, and mRNA decay (Nott et al (2003) RNA 9:607-617). Within the context of mRNA expression, there has been no bright line of predictability regarding the result of an intron on the yield of protein from a vector. For example, it has been variously reported that including various intronic sequences can cause large increases in expression, have no effect, or reduce mRNA expression (Berg et al. (1988) *Mol. Cell. Biol.* 8:4395-4405; Bourdon et al. (2001) *EMBO Rep.* 2:394-398). Since most higher eukaryotic genes contain introns, the development of a system which may be used to predictably express intron-containing genes at high levels and with close fidelity to the exonic sequences of the gene in the absence of unwanted read-through by products is obviously an aid to the predictable development of protein expression systems.

While the unpredictability associated with intronic sequences poses a hurdle to reliable expression vector design, a significant design benefit can be realized when the protein of interest has a modular form which is amenable to genetic engineering techniques. Antibodies provide one such example wherein the inclusion of intronic sequences facilitates expression vector design.

Certain terms used in the specification and claims are defined below.

The phrase "intron read-through" ("IRT") denotes the process whereby aberrant splicing of a pre-mRNA transcript yields a protein or peptide of alternate size or amino acid constituency. Varying results may occur concerning the ultimate protein produced from the mis-spliced transcript. For example, a larger than predicted protein or a protein with an incorrect stop codon may occur, in which case the protein may be longer or shorter than predicted, respectively. Further, the protein may also have incorrect or additional residues facilitating protein modification for glycosylation, myristoylation, phosphorylation, ubiquitination, or other post-translational modifications.

The term "intron read-through by-product" refers to proteins or peptides that are translated from aberrantly-spliced mRNA resulting from intron read-through, e.g., proteins of unpredicted size or amino acid constituency. Intron read-through by products may be shorter or longer than the polypeptides predicted by the genes known amino acid sequence and/or predicted by the cDNA of the gene. Intron read-through by products may also have apparent molecular weights differing from the accepted molecular weight of proteins arising from the correctly spliced mRNA of the gene. Further, the term "intron read-through by-products" includes proteins that occur from proteolytic processing events not normally associated with the protein of interest, said proteolytic processing arising potentially from frame shifted protein products due to read through of an intron-exon-junction.

The term "heavy chain by-product" refers to polypeptides that are translated from aberrantly spliced immunoglobulin heavy chain mRNA resulting from intron read-through, e.g. a heavy chain protein of unpredicted size or amino acid constituency. Heavy chain byproducts may be shorter or longer than the polypeptide predicted by the immunoglobulin gene's known amino acid sequence and/or predicted by the cDNA of the gene. Heavy chain by-products may also have apparent molecular weights differing from the accepted molecular weight of proteins arising from the correctly spliced mRNA of the heavy chain gene. Further, the term "heavy chain by-products" includes polypeptides that occur from proteolytic processing events not normally associated with the protein.

The phrase "naturally-occurring sequence" or "naturally-occurring genomic sequence" refers to the intronic and exonic organization of a gene found in its natural or native state. The naturally-occurring sequence can be found in, e.g., its natural chromosomal location or cloned into a vector, so long as the intronic and exonic organization of the sequence is retained.

The term "immunoglobulin" or "antibody" (used interchangeably herein) refers to a protein having a four-polypeptide chain structure consisting of two heavy and two light chains, said chains being stabilized, for example, by interchain disulfide bonds, wherein the immunoglobulin or antibody has the ability to specifically bind an antigen.

The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, wherein the immunoglobulin or antibody has has the ability to specifically bind antigen.

The term "immunoglobulin or antibody domain" refers to a globular region within a heavy or light chain polypeptide including peptide loops (e.g., including 3 to 4 peptide loops) stabilized, for example, by β-pleated sheet and/or intrachain disulfide bond. Domains are further referred to herein as "constant" or "variable" wherein the term "constant" refers to the relative lack of sequence variation within the domains of various class members in the case of a "constant" domain and wherein the term "variable" refers to the significant variation within the domains of various class members in the case of a "variable" domain. Antibody or polypeptide "domains" are often referred to interchangeably in the art as antibody or polypeptide "regions." The "constant" domains of an antibody light chain are referred to interchangeably as "light chain constant regions," "light chain constant domains," "CL" regions or "CL" domains. The "constant" domains of an antibody heavy chain are referred to interchangeably as "heavy chain constant regions," "heavy chain constant domains," "CH" regions or "CH" domains. The "variable" domains of an antibody light chain are referred to interchangeably as "light chain variable regions," "light chain variable domains," "VL" regions or "VL" domains. The "variable" domains of an antibody heavy chain are referred to interchangeably as "heavy chain constant regions," "heavy chain constant domains," "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

Immunoglobulins or antibodies can exist in monomeric or polymeric form, for example, IgM antibodies, which exist in pentameric form, and/or IgA antibodies, which exist in monomeric, dimeric or multimeric form. The term "fragment" refers to a part or portion of an antibody or antibody chain including fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fabc, and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof. The term "conformation" may also refer to quaternary structures resulting from the the three dimensional relationship of one or several proteins or peptide chains. In relation to antigenic determinants, the phrase "conformational epitope" refers to an antigenic determinant including a specific spatial arrangement of amino acids within one or several proteins existing in close apposition. Considering the multifunctional nature of antibodies (i.e. the ability of IgG molecules to bind several epitopes concomitantly on more than one protein molecule), antibodies can be considered as having the innate ability to bind conformational epitopes comprised by several amino acid chains. For example, the deposition of Aβ to form plaques provides a conformational epitope in which one antibody may bind several closely positioned Aβ peptides.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "significant identity" means that two sequences, e.g., two polypeptide sequences, when optimally aligned, such as by the programs GAβ or BESTFIT using default gap weights, share at least 50-60% sequence identity, preferably at least 60-70% sequence identity, more preferably at least 70-80% sequence identity, more preferably at least 80-90% identity, even more preferably at least 90-95% identity, and even more preferably at least 95% sequence identity or more (e.g., 99% sequence identity or more). The term "substantial identity" or "substantially identical" means that two sequences, e.g., two polypeptide sequences, when optimally aligned, such as by the programs GAP or BESTFIT using default gap weights, share at least 80-90% sequence identity, preferably at least 90-95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Antibodies

The methodologies of the present invention are applicable in a variety of antibody production processes where unwanted or undesirable by-products are detected. In particular, the methodologies are applicable in production of recombinant antibodies, such as chimeric and humanized monoclonal antibodies, where the sequence of the antibody being produced is known.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, back-mutations, and the like. The introduction of conservative substitutions, consensus sequence substitutions, germline substitutions, back-mutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

Preferably, humanized immunoglobulins or antibodies bind antigen with an affinity that is within a factor of three, four, or five of that of the corresponding non-humanized antibody. For example, if the non-humanized antibody has a binding affinity of $10^9$ $M^{-1}$, humanized antibodies will have a binding affinity of at least $3\times10^9$ $M^{-1}$, $4\times10^9$ $M^{-1}$, or $5\times10^9$ $M^{-1}$. When describing the binding properties of an immunoglobulin or antibody chain, the chain can be described based on its ability to "direct antigen (e.g., Aβ or 5T4) binding." A chain is said to "direct antigen binding" when it confers upon an intact immunoglobulin or antibody (or antigen binding fragment thereof) a specific binding property or binding affinity. A mutation (e.g., a back-mutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined herein. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

Monoclonal, chimeric and humanized antibodies, which have been modified, e.g., by deleting, adding, or substituting other portions of the antibody, e.g., the constant region, are also within the scope of the invention. For example, an antibody can be modified as follows: (i) by replacing the constant region with another constant region, e.g., a constant region meant to increase half-life, stability or affinity of the antibody, or a constant region from another species or antibody class; or (ii) by modifying one or more amino acids in the constant region to alter, for example, the number of glycosylation sites, effector cell function, Fc receptor (FcR) binding, complement fixation, among others. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624, 821).

Human Antibodies From Transgenic Animals and Phage Display

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice results in the production of human antibodies upon antigen challenge. See, e.g., U.S. Pat. Nos. 6,150,584; 6,114,598; and 5,770,429.

Fully human antibodies can also be derived from phage-display libraries (Hoogenboom et al, J. Mol. Biol., 227:381 (1991); Marks et al., J. Mol. Biol., 222:581-597 (1991)).

Bispecific Antibodies, Antibody Fusion Polypeptides, and Single-Chain Antibodies Bispecific antibodies (BsAbs) are antibodies that have binding specificities for at least two different epitopes. Such antibodies can be derived from full length antibodies or antibody fragments (e.g. F(ab)'$_2$ bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another embodiment, the antibody can be fused, chemically or genetically, to a payload domain, for example, an immunotoxin to produce an antibody fusion polypeptide. Such payloads include, for example, immunotoxins, chemotherapeutics, and radioisotopes, all of which are well-known in the art.

Single chain antibodies are also suitable for stabilization according to the invention. The fragments comprise a heavy-chain variable domain (VH) connected to a light-chain variable domain (VL) with a linker, which allows each variable region to interface with each other and recreate the antigen binding pocket of the parent antibody from which the VL and VH regions are derived. See Gruber et al., J. Immunol., 152: 5368 (1994).

Anti-Aβ Antibodies

Generally, the antibodies of the present invention include antibodies for treating amyloidogenic diseases, in particular, Alzheimer's Disease, by targeting Aβ peptide.

The term "amyloidogenic disease" includes any disease associated with (or caused by) the formation or deposition of insoluble amyloid fibrils. Exemplary amyloidogenic diseases include, but are not limited to, systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ," e.g., in the brain of a subject or patient. The terms "β-amyloid protein," "β-amyloid peptide," "β-amyloid," "Aβ," and "Aβ peptide" are used interchangeably herein.

An "immunogenic agent" or "immunogen" is capable of inducing an immunological response against itself on administration to a mammal, optionally in conjunction with an adjuvant.

The terms "Aβ antibody," "anti Aβ antibody," and "anti Aβ" are used interchangeably herein to refer to an antibody that binds to one or more epitopes or antigenic determinants of APP, Aβ protein, or both. Exemplary epitopes or antigenic determinants can be found within the human amyloid precursor protein (APP), but are preferably found within the Aβ peptide of APP. Multiple isoforms of APP exist, for example APP$^{695}$, APP$^{751}$, and APP$^{770}$. Amino acids within APP are assigned numbers according to the sequence of the APP$^{770}$ isoform (see e.g., GenBank Accession No. P05067). Aβ (also referred to herein as beta amyloid peptide and A beta) peptide is a ~4-kDa internal fragment of 39-43 amino acids of APP (Aβ39, Aβ40, Aβ41, Aβ42, and Aβ43). Aβ40, for example, consists of residues 672-711 of APP and Aβ42 consists of residues 672-713 of APP. As a result of proteolytic processing of APP by different secretase enzymes iv vivo or in situ, Aβ is found in both a "short form," 40 amino acids in length, and a "long form," ranging from 42-43 amino acids in length. Epitopes or antigenic determinants can be located within the N-terminus of the Aβ peptide and include residues within amino acids 1-10 of Aβ, preferably from residues 1-3, 1-4, 1-5, 1-6, 1-7, 2-7, 3-6, or 3-7 of Aβ42 or within residues 2-4, 5, 6, 7, or 8 of Aβ, residues 3-5, 6, 7, 8, or 9 of Aβ, or residues 4-7, 8, 9, or 10 of Aβ42. "Central" epitopes or antigenic determinants are located within the central or mid-portion of the Aβ peptide and include residues within amino acids 16-24, 16-23, 16-22, 16-21, 19-21, 19-22, 19-23, or 19-24 of Aβ. "C-terminal" epitopes or antigenic determinants are located within the C-terminus of the Aβ peptide and include residues within amino acids 33-40, 33-41, or 33-42 of Aβ.

In various embodiments, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP.

In various embodiments, an Aβ antibody is "C-terminus-specific." As used herein, the term "C terminus-specific" means that the antibody specifically recognizes a free C-terminus of an Aβ peptide. Examples of C terminus-specific Aβ antibodies include those that: recognize an Aβ peptide ending at residue 40, but do not recognize an Aβ peptide ending at residue 41, 42, and/or 43; recognize an Aβ peptide ending at residue 42, but do not recognize an Aβ peptide ending at residue 40, 41, and/or 43; etc.

In one embodiment, the antibody may be a 3D6 antibody or variant thereof, or a 10D5 antibody or variant thereof, both of which are described in U.S. Patent Publication No. 2003/0165496A1, U.S. Patent Publication No. 2004/0087777A1, International Patent Publication No. WO02/46237A3. Description of 3D6 and 10D5 can also be found, for example, in International Patent Publication No. WO02/088306A2 and International Patent Publication No. WO02/088307A2. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. In another embodiment, the antibody may be a 12B4 antibody or variant thereof, as described in U.S. Patent Publication No. 20040082762A1 and International Patent Publication No. WO03/077858A2. 12B4 is a mAb that specifically binds to an N-terminal epitope located in the human β-amyloid peptide, specifically, residues 3-7. In yet another embodiment, the antibody may be a 12A11 antibody or a variant thereof, as described in U.S. patent application Ser. No. 10/858,855 and International Patent Application No. PCT/US04/17514. 12A11 is a mAb that specifically binds to an N-terminal epitope located in the human β-amyloid peptide, specifically, residues 3-7. In yet another embodiment, the antibody may be a 266 antibody as described in U.S. patent application Ser. No. 10/789,273, and International Patent Application No. WO01/62801A2. Antibodies designed to specifically bind to C-terminal epitopes located in human β-amyloid peptide, for use in the present invention include, but are not limited to, 369.2B, as described in U.S. Pat. No. 5,786,160.

In exemplary embodiments, the antibody is a humanized anti Aβ peptide 3D6 antibody that selectively binds Aβ peptide. More specifically, the humanized anti Aβ peptide 3D6 antibody is designed to specifically bind to an $NH_2$-terminal epitope located in the human β-amyloid 1-40 or 1-42 peptide found in plaque deposits in the brain (e.g., in patients suffering from Alzheimer's disease).

Anti-5T4 Antibodies

The 5T4 antigen has been previously characterized (see e.g., WO 89/07947). The full nucleic acid sequence of human 5T4 is known (Myers et al. (1994) *J Biol Chem* 169: 9319-24 and GenBank at Accession No. Z29083). The sequence for 5T4 antigen from other species is also known, for example, murine 5T4 (WO00/29428), canine 5T4 (WO01/36486) or feline 5T4 (US 05/0100958).

Human 5T4 is a glycoprotein of about 72 kDa expressed widely in carcinomas, but having a highly restricted expression pattern in normal adult tissues. It appears to be strongly correlated to metastasis in colorectal and gastric cancer. Expression of the 5T4 antigen is also found at high frequency in breast and ovarian cancers (Starzynska et al. (1998) *Eur. J. Gastroenterol. Hepatol.* 10:479-84; Starzynska et al. (1994) *Br. J. Cancer* 69:899-902; Starzynska et al. (1992) *Br. J. Cancer* 66:867-9). 5T4 has been proposed as a marker, with possible mechanistic involvement, for tumor progression and metastasis potential (Carsberg et al. (1996) *Int J Cancer* 68:84-92). 5T4 has also been proposed for use as an immunotherapeutic agent (see WO 00/29428). Antigenic peptides of 5T4 are disclosed in, e.g., US 05/0100958, the contents of which are incorporated by reference.

Several pending applications relate generally to nucleic acids encoding the anti-5T4 monoclonal antibody, vectors and host cells thereof, for example, U.S. Application Publication Nos. 2003/0018004 and 2005/0032216 and U.S. application Ser. No. 10/016,686. A provisional patent application pertaining generally to the humanized anti-5T4 H8 monoclonal antibodies and calicheamicin conjugates thereof, as well as methods of treatment using these calicheamicin conjugates has been filed (U.S. Application Ser. No. 60/608,494). The contents of all of these applications are incorporated by reference herein in their entirety.

Fc Fusions

In some embodiments, the nucleic acid molecules of the invention encode a fusion or a chimeric protein. The fusion protein can include a targeting moiety, e.g., a soluble receptor fragment or a ligand, and an immunoglobulin chain, an Fc fragment, a heavy chain constant regions of the various isotypes, including: IgG1, IgG2, IgG3, IgG4, IgM, IgA1, IgA2, IgD, and IgE). For example, the fusion protein can include the extracellular domain of a receptor, and, e.g., fused to, a human immunoglobulin Fc chain (e.g., human IgG, e.g., human IgG1 or human IgG4, or a mutated form thereof). In one embodiment, the human Fc sequence has been mutated at one or more amino acids, e.g., mutated at residues 254 and 257 from the wild type sequence to reduce Fc receptor binding. The fusion proteins may additionally include a linker sequence joining the first moiety to the second moiety, e.g., the immunoglobulin fragment. For example, the fusion protein can include a peptide linker, e.g., a peptide linker of about 4 to 20, more preferably, 5 to 10, amino acids in length; the peptide linker is 8 amino acids in length. For example, the fusion protein can include a peptide linker having the formula (Ser-Gly-Gly-Gly-Gly)y wherein y is 1, 2, 3, 4, 5, 6, 7, or 8. In other embodiments, additional amino acid sequences can be added to the N— or C-terminus of the fusion protein to facilitate expression, steric flexibility, detection and/or isolation or purification.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that encode a fusion moiety (e.g., an Fc region of an immunoglobulin heavy chain). Immunoglobulin fusion polypeptide are known in the art and are described in e.g., U.S. Pat. Nos. 5,516,964; 5,225,538; 5,428,130; 5,514,582; 5,714,147; and 5,455,165.

Nucleic Acid Molecules, Constructs and Vectors

Exemplary embodiments of the instant invention feature engineered constructs designed to eliminate unwanted or undesirable by-products, in particular, unwanted or undesirable antibody (or immunoglobulin) by-products. In certain aspects, the constructs include components of naturally-occurring antibody gene sequences, wherein the components have been genetically altered, modified, or engineered (e.g., genetically engineered) such that the resultant construct expresses the desired protein (e.g., antibody) of interest in the absence of the unwanted or undesired by-product. Constructs can be generated using art-recognized techniques for producing recombinant nucleic acid molecules (e.g., comprising components of immunoglobulin chain genes) as described in detail below.

Antibody gene sequences encode antibodies of the various isotypes, including: IgG (e.g., IgG1, IgG2, IgG3, IgG4), IgM, IgA1, IgA2, IgD, or IgE. Preferably, the antibody gene sequences encodes an antibody of the antibody is an IgG isotype. The encoded immunoglobulin or antibody molecules can include full-length (e.g., an IgG1 or IgG4 immunoglobulin) or alternatively can include only a fragment (e.g., a Fc fragment).

It will be appreciated by the skilled artisan that nucleotide sequences encoding the antibodies of the instant invention can be derived from the nucleotide and amino acid sequences described in the present application or from additional sources of sequences of immunoglobulin genes known in the art using the genetic code and standard molecular biology techniques. The nucleic acid compositions of the present invention may be derived from known immunoglobulin DNA (e.g., cDNA sequences). In particular, nucleotide sequences may be substantially identical to or derived from native V, D, J, or constant cDNA sequences. The sequences of heavy and light chain constant region genes are known in the art. Preferably, the constant region is human, but constant regions from other species, e.g., rodent (e.g., mouse or rat), primate (macaque), camel, or rabbit, can also be used. Constant regions from these species are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. Sequences for heavy chain constant regions are known in the art and can be found in, e.g., NCBI NG_001019. In typical embodiments, the constant region is an IgG1 or IgG4 constant region. For an Fc fragment heavy chain gene, the Fc-encoding DNA can be operatively linked to a heavy chain leader sequence (e.g., a heavy chain variable chain leader sequence) for direct expression.

Additional aspects of the invention include assembled immunoglobulin DNA cassette sequences. Assembled immunoglobulin cassette sequences include nucleotide sequences as well as amino acid sequences encoded by an immunoglobulin DNA cassette nucleotide sequence.

An exemplary human IgG1 constant region genomic sequence is hereby provided:

```
GTGAGTCCTGTCGACTCTAGAGCTTTCTGGGGCAGGCCAGGCCTGACTTTGGCTGGGGG  (SEQ ID NO:1)
CAGGGAGGGGGCTAAGGTGACGCAGGTGGCGCCAGCCAGGCGCACACCCAATGCCCATG
AGCCCAGACACTGGACGCTGAACCTCGCGGACAGTTAAGAACCCAGGGGCCTCTGCGCC
CTGGGCCCAGCTCTGTCCCACACCGCGGTCACATGGCACCACCTCTCTTGCAGCCTCCA
CCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACCCAGACCTAC
ATCTGCAACGTGAATCACAAGCCCAGCAACACCAAGGTGGACAAGAAAGTTGGTGAGAG
GCCAGCACAGGGAGGGAGGGTGTCTGCTGGAAGCCAGGCTCAGCGCTCCTGCCTGGACG
CATCCCGGCTATGCAGTCCCAGTCCAGGGCAGCAAGGCAGGCCCCGTCTGCCTCTTCAC
CCGGAGGCCTCTGCCCGCCCCACTCATGCTCAGGGAGAGGGTCTTCTGGCTTTTTCCCC
AGGCTCTGGGCAGGCACAGGCTAGGTGCCCCTAACCCAGGCCCTGCACACAAAGGGGCA
GGTGCTGGGCTCAGACCTGCCAAGAGCCATATCCGGGAGGACCCTGCCCCTGACCTAAG
CCCACCCCAAAGGCCAAACTCTCCACTCCCTCAGCTCGGACACCTTCTCTCCTCCCAGA
TTCCAGTAACTCCCAATCTTCTCTCTGCAGAGCCCAAATCTTGTGACAAAACTCACACA
TGCCCACCGTGCCCAGGTAAGCCAGCCCAGGCCTCGCCCTCCAGCTCAAGGCGGGACAG
GTGCCCTAGAGTAGCCTGCATCCAGGGACAGGCCCCAGCCGGGTGCTGACACGTCCACC
TCCATCTCTTCCTCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGGAGGTG
CATAATGCCAAGACAAAGCCGCGGGAGGAGCAGTACAACAGCACGTACCGTGTGGTCAG
CGTCCTCACCGTCCTGCACCAGGACTGGCTGAATGGCAAGGAGTACAAGTGCAAGGTCT
CCAACAAAGCCCTCCCAGCCCCCATCGAGAAAACCATCTCCAAAGCCAAAGGTGGGACC
CGTGGGGTGCGAGGGCCACATGGACAGAGGCCGGCTCGGCCCACCCTCTGCCCTGAGAG
TGACCGCTGTACCAACCTCTGTCCCTACAGGGCAGCCCCGAGAACCACAGGTGTACACC
CTGCCCCCATCCCGGGAGGAGATGACCAAGAACCAGGTCAGCCTGACCTGCCTGGTCAA
AGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTATAGCAAG
CTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCCCCGGGTAAATGA
```

An exemplary IgG4 constant region genomic sequence is hereby provided:

```
GTGAGTCCTGTCGACTCTAGAGCTTTCTGGGGCAGGCCAGGCCTGACTTTGGCTGGGGG  (SEQ ID NO:3)
CAGGGAGGGGGCTAAGGTGACGCAGGTGGCGCCAGCCAGGCGCACACCCAATGCCCATG
AGCCCAGACACTGGACGCTGAACCTCGCGGACAGTTAAGAACCCAGGGGCCTCTGCGCC
CTGGGCCCAGCTCTGTCCCACACCGCGGTCACATGGCACCACCTCTCTTGCAGCCTCCA
CCAAGGGCCCATCGGTCTTCCCCCTGGCGCCCTGCTCCAGGAGCACCTCCGAGAGCACA
GCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACGAAGACCTAC
ACCTGCAATGTAGATCACAAGCCCAGCAACACCAAGGTGGACAAGAGAGTTGGTGAGAG
GCCAGCACAGGGAGGGAGGGTGTCTGCTGGAAGCCAGGCTCAGCCCTCCTGCCTGGACG
CACCCCGGCTGTGCAGCCCCAGCCCAGGGCAGCAAGGCAGGCCCCATCTGTCTCCTCAC
CTGGAGGCCTCTGACCACCCCACTCATGCTCAGGGAGAGGGTCTTCTGGATTTTTCCAC
CAGGCTCCGGGCAGCCACAGGCTGGATGCCCCTACCCCAGGCCCTGCGCATACAGGGGC
AGGTGCTGCGCTCAGACCTGCCAAGAGCCATATCCGGGAGGACCCTGCCCCTGACCTAA
GCCCACCCCAAAGGCCAAACTCTCCACTCCCTCAGCTCAGACACCTTCTCTCCTCCCAG
ATCTGAGTAACTCCCAATCTTCTCTCTGCAGAGTCCAAATATGGTCCCCCATGCCCACC
ATGCCCAGGTAAGCCAACCCAGGCCTCGCCCTCCAGCTCAAGGCGGGACAGGTGCCCTA
GAGTAGCCTGCATCCAGGGACAGGCCCCAGCCGGGTGCTGACGCATCCACCTCCATCTC
```

```
                              -continued
TTCCTCAGCACCTGAGTTCCTGGGGGGACCATCAGTCTTCCTGTTCCCCCCAAAACCCA
AGGACACTCTCATGATCTCCCGGACCCCTGAGGTCACGTGCGTGGTGGTGGACGTGAGC
CAGGAAGACCCCGAGGTCCAGTTCAACTGGTACGTGGATGGCGTGGAGGTGCATAATGC
CAAGACAAAGCCGCGGGAGGAGCAGTTCAACAGCACGTACCGTGTGGTCAGCGTCCTCA
CCGTCCTGCACCAGGACTGGCTGAACGGCAAGGAGTACAAGTGCAAGGTCTCCAACAAA
GGCCTCCCGTCCTCCATCGAGAAAACCATCTCCAAAGCCAAAGGTGGGACCCACGGGGT
GCGAGGGCCACATGGACAGAGGTCAGCTCGGCCCACCCTCTGCCCTGGGAGTGACCGCT
GTGCCAACCTCTGTCCCTACAGGGCAGCCCCGAGAGCCACAGGTGTACACCCTGCCCCC
ATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAGGCTAACCGT
GGACAAGAGCAGGTGGCAGGAGGGGAATGTCTTCTCATGCTCCGTGATGCATGAGGCTC
TGCACAACCACTACACACAGAAGAGCCTCTCCCTGTCTCTGGGTAAATGA
```

Antibody Production

Antibodies of the present invention are typically produced by recombinant expression. Nucleic acids encoding light and heavy chains can be inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells (e.g., COS or CHO cells).

Following manipulation of the isolated genetic material to provide polypeptides of the invention as set forth above, the genes are typically inserted in an expression vector for introduction into host cells that may be used to produce the desired quantity of modified antibody that, in turn, provides the claimed polypeptides. The term "vector" includes a nucleic acid construct often including a nucleic acid, e.g., a gene, and further including minimal elements necessary for nucleic acid replication, transcription, stability and/or protein expression or secretion from a host cell. Such constructs may exist as extrachromosomal elements or may be integrated into the genome of a host cell.

The term "expression vector" includes a specific type of vector wherein the nucleic acid construct is optimized for the high-level expression of a desired protein product. Expression vectors often have transcriptional regulatory agents, such as promoter and enhancer elements, optimized for high-levels of transcription in specific cell types and/ or optimized such that expression is constitutive based upon the use of a specific inducing agent. Expression vectors further have sequences that provide for proper and/or enhanced translation of the protein As known to those skilled in the art, such vectors may easily be selected from the group consisting of plasmids, phages, viruses, and retroviruses. The term "expression cassette" includes a nucleic acid construct containing a gene and having elements in addition to the gene that allow for proper and or enhanced expression of that gene in a host cell.

The term "operably linked" includes a juxtaposition wherein the components are in a relationship permitting them to function in their intended manner (e.g., functionally linked). As an example, a promoter/enhancer operably linked to a polynucleotide of interest is ligated to said polynucleotide such that expression of the polynucleotide of interest is achieved under conditions which activate expression directed by the promoter/enhancer. In regards to the invention described herein, operably linked also encompasses the relationship of splice donor and splice acceptor sites found in the primary transcript (pre-mRNA) of a gene of interest. Normally, splice acceptor and donor sites are operably linked in that the two sequences are required and function together for splicing events to occur resulting in a mature messenger RNA.

Expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362). In addition to the immunoglobulin DNA cassette sequences, insert sequences, and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Once the vector has been incorporated into the appropriate host, the host is maintained under conditions suitable for high level expression of the nucleotide sequences, and the collection and purification of the desired antibodies. Mammalian cells are preferred for expression and production of the antibodies of the present invention. See, e.g., Winnacker, *From Genes to Clones*, VCH Publishers, N.Y., N.Y. (1987). Eukaryotic cells are preferred because a number of suitable host cell lines capable of secreting heterologous proteins (e.g., intact immunoglobulins) have been developed in the art, and include CHO cell lines, various COS cell lines, HeLa cells, preferably, myeloma cell lines, or transformed B-cells or hybridomas. Preferably, the cells are non-human. Preferred mammalian host cells for expressing the antibodies of the invention include Chinese Hamster Ovary (CHO cells) (including dhfr CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and cells derived from a transgenic animal, e.g., mammary epithelial cell. Other suitable host cells are known to those skilled in the art.

Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See, e.g., Co et al., (1992) *J. Immunol.* 148:1149. Preferred regulatory sequences for mammalian host cell expression include viral elements that direct high levels of protein expression in mammalian cells, such as promoters and/or enhancers derived from FF-1a promoter and BGH poly A, cytomegalovirus (CMV) (such as the CMV promoter/enhancer), Simian Virus 40 (SV40) (such as the SV40 promoter/enhancer), adenovirus (e.g., the adenovirus major late promoter (AdMLP)), and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al. In exemplary embodiments, the antibody heavy and light chain genes are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. In exemplary embodiments of the invention, the construct include an internal ribosome entry site (IRES) to provide relatively high levels of polypeptides of the invention in eukaryotic host cells. Compatible IRES sequences are disclosed in U.S. Pat. No. 6,193,980 that is also incorporated herein.

Alternatively, antibody-coding sequences can be incorporated in a transgene for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Prokaryotic host cells may also be suitable for producing the antibodies of the invention. *E. coli* is one prokaryotic host particularly useful for cloning the polynucleotides (e.g., DNA sequences) of the present invention. Other microbial hosts suitable for use include bacilli, such as *Bacillus subtilis*, enterobacteriaceae, such as *Escherichia, Salmonella*, and *Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Expression of proteins in prokaryotes is most often carried out in *E. coli* with vectors containing constitutive or inducible promoters directing the expression of either fusion or non-fusion proteins. Fusion vectors add a number of amino acids to an antibody encoded therein, often to the constant region of the recombinant antibody, without affecting specificity or antigen recognition of the antibody. Addition of the amino acids of the fusion peptide can add additional function to the antibody, for example as a marker (e.g., epitope tag such as myc or flag).

Other microbes, such as yeast, are also useful for expression. Saccharomyces is a preferred yeast host, with suitable vectors having expression control sequences (e.g., promoters), an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Alternatively, antibodies of the invention can be produced in transgenic plants (e.g., tobacco, maize, soybean and alfalfa). Improved 'plantibody' vectors (Hendy et al. (1999) *J. Immunol. Methods* 231:137-146) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials and therefore the risk of contamination with a transmissible spongiform encephalopathy (TSE) agent. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see, e.g., Larrick et al. (1998) *Res. Immunol.* 149:603-608).

Various methods may be used to express recombinant antibodies in transgenic plants. For example, antibody heavy and light chains can be independently cloned into expression vectors (e.g., *Agrobacterium tumefaciens* vectors), followed by the transformation of plant tissue in vitro with the recombinant bacterium or direct transformation using, e.g., particles coated with the vector which are then physically introduced into the plant tissue using, e.g., ballistics. Subsequently, whole plants expressing individual chains are reconstituted followed by their sexual cross, ultimately resulting in the production of a fully assembled and functional antibody. Similar protocols have been used to express functional antibodies in tobacco plants (see, e.g., Hiatt et al. (1989) *Nature* 342:76-87). In various embodiments, signal sequences may be utilized to promote the expression, binding and folding of unassembled antibody chains by directing the chains to the appropriate plant environment (e.g., the aqueous environment of the apoplasm or other specific plant tissues including tubers, fruit or seed) (see Fiedler et al. (1995) *Bio/Technology* 13:1090-1093). Plant bioreactors can also be used to increase antibody yield and to significantly reduce costs.

Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual (Cold Spring Harbor Press*, 2nd ed., 1989), incorporated by reference herein in its entirety for all purposes.) Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

An immunoglobulin or antibody produced according to the instant invention molecule can be derivatized or linked to another functional molecule (e.g., another peptide or protein). Accordingly, the antibodies and antibody portions or otherwise modified forms of the antibodies of the invention described herein, may be further derivatized for use in research, diagnostic and/or therapeutic contexts. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Exemplary fluorescent detectable agents include fluorescein, fluorescein isothiocyanate, rhodamine, 5-dimethylamine-1-napthalenesulfon-yl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{111}I$, $^{35}S$ or $^{3}H$. An antibody (or fragment thereof) may also be conjugated to a therapeutic moiety such as a cytotoxin or other therapeutic protein. Alternatively, an antibody can be conjugated to a second antibody to form an antibody heteroconjugate as described by Segal in U.S. Pat. No. 4,676,980.

Expression Vectors for Decreasing or Eliminating Unwanted Polypeptide By-Products During the development of a protein expression system for therapeutic proteins, HPLC analysis of purified target product identified unexpected low molecular weight (LMW) species of peptides. More specifically, undesired polypeptide by-products were observed in a CHO (Chinese hamster ovary) cell line developed to express the 3D6 antibody. This antibody has been described elsewhere and is the result of efforts to develop an immunotherapeutic agent useful for the treatment of Alzheimer's disease. It has specificity for the A-beta peptide and has been demonstrated to be efficacious in clearing A-beta plaques. The CHO cell line was developed using art accepted methods and contained copies of the heavy and light chain of the 3D6 antibody in addition to genes for selective culture of expression cassette containing cells.

Examination of a number of clonal isolates of the cell line demonstrated that production of the LMW species was not a phenomenon specific to the clone being utilized, i.e., a minor fraction of the total protein produced in all of the cell lines tested was of the unexpected LMW species. It was further observed that the fraction of LMW species relative to total protein increased when protein expression was induced. Further evaluation of the polypeptides using mass spectrometry indicated that the LMW species contained amino acids not predicted by the exonic sequences of the gene.

The top panel of FIG. 1 schematically presents the 3D6 heavy chain expression cassette showing the relation of introns and exons as well as the position of the internal ribosomal entry site (IRES) and dihydrofolate reductase (DHFR) selectable marker gene. The exons shown are variable heavy ($V_H1$), hinge and constant heavy 1, 2 and 3 ($C_H1$, $C_H2$, $C_H3$). The introns of the expression cassette are denoted Int1, Int2, Int3 and Int4. FIG. 1 further illustrates the predicted correct splicing events for the mRNA derived from the expression cassette. The middle panel shows the correctly spliced mRNA containing only intronic sequences of the bicistronic transcript.

Scrutiny of the intronic and exonic sequences in the expression vector and mass spectrometry data pointed to RNA polymerase intron read-through (IRT) of a specific splice site junction. Since the organization of the introns and exons and splice site donor and acceptor sites contained in the expression vector were substantially identical to those as they existed in the original genomic form of the gene, the miss-plicing event was not predictable.

Figure 2:
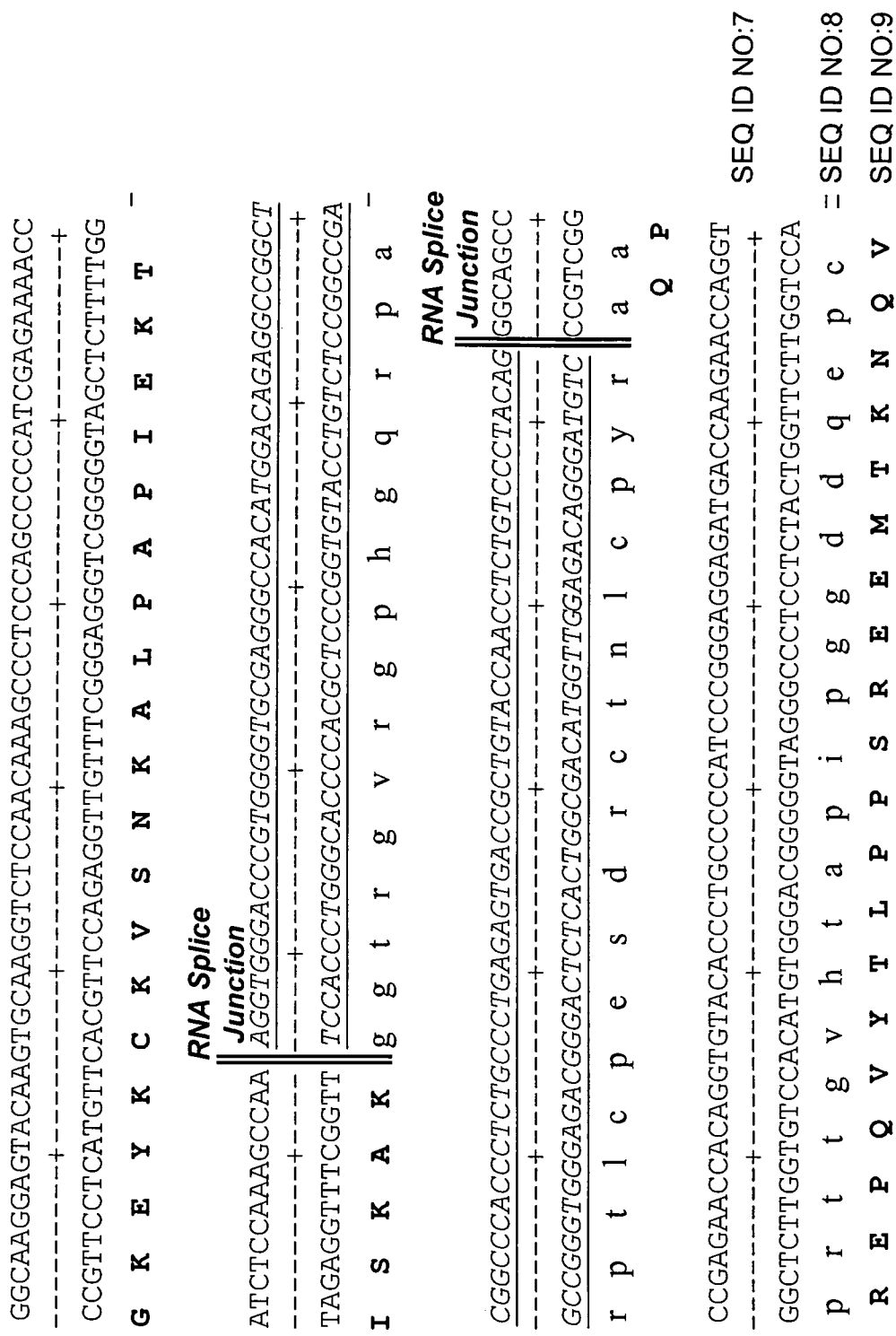
FIG. 2 shows the nucleic acid sequence spanning the intron between the CH2 and CH3 constant regions (referred to as the fourth intron) of the 3D6 heavy-chain expression vector indicating genomic 5' and 3' splice junctions (SEQ ID NO:7). Also shown is the predicted partial amino acid sequence of the polypeptides derived from correctly (SEQ ID NO:8) and incorrectly (SEQ ID NO:9) spliced mRNA. The RNA splice junctions are indicated by a solid double line.

The bottom panel of FIG. 1 illustrates the predicted product generated by intron read-through of the fourth intron. FIG. 2 provides sequence information showing the sense and anti-sense strands of the DNA sequence in the region of the fourth intron of the genomic sequence of the 3D6 antibody expression vector. The splice junctions (splice donor and acceptor sites) are denoted by vertical lines perpendicular to the nucleic acid sequence. DNA corresponding to intronic sequence is shown underlined and in italics. Predicted amino acids for desired and read-through by-product polypeptides are shown below the anti-sense strand of the genomic DNA. The amino acid sequence of polypeptide derived from correctly spliced RNA is shown in bold uppercase lettering; polypeptide by-products derived from incorrectly spliced RNA is shown in lowercase font.

The present invention describes materials and methods for designing protein expression cassettes and vectors such that intron read-through (IRT) and unwanted polypeptide byproducts are substantially reduced or eliminated entirely. In part, the invention provides on the novel design of vectors wherein the natural operative association of introns and exons in an isolated nucleic acid coding for a protein of interest are altered such that IRT is reduced or eliminated thereby reducing or eliminating unwanted IRT polypeptide species. The unique alterations are particularly suitable for IgG1 or IgG4 antibodies, but may be used for any gene of interest. Moreover the vectors of the instant invention having introns and exons with altered natural operative associations demonstrate not only reduced or eliminated IRT by-products but also increased protein expression levels relative to vectors designed using standard art recognized techniques.

EXAMPLES

Materials and Methods

Throughout the examples, materials and methods as exemplified in the following texts were used unless otherwise stated:

In general, the practice of the present invention employs art-recognized techniques in molecular biology, recombinant DNA technology, and immunology especially, e.g. antibody technology. See, e.g., Sambrook, Fritsch and Maniatis, Molecular Cloning: Cold Spring Harbor laboratory Press (1989); Antibody Engineering Protocols (Methods in Molecular Biology), 510, Paul, S., Human Press (1996); Antibody Engineering: A Practical Approach (Practical Approach Series, 169), McCafferty, Ed IRL Press (1996); Antibodies: A Laboratory Manual, Harlow et al Cold Spring Harbor Press, (1999); and Current Protocols in Molecular Biology eds. Ausubel et al John Wiley & Sons (1992).

Example 1

Quantification of Intron Read-Through Transcription

Figure 3:
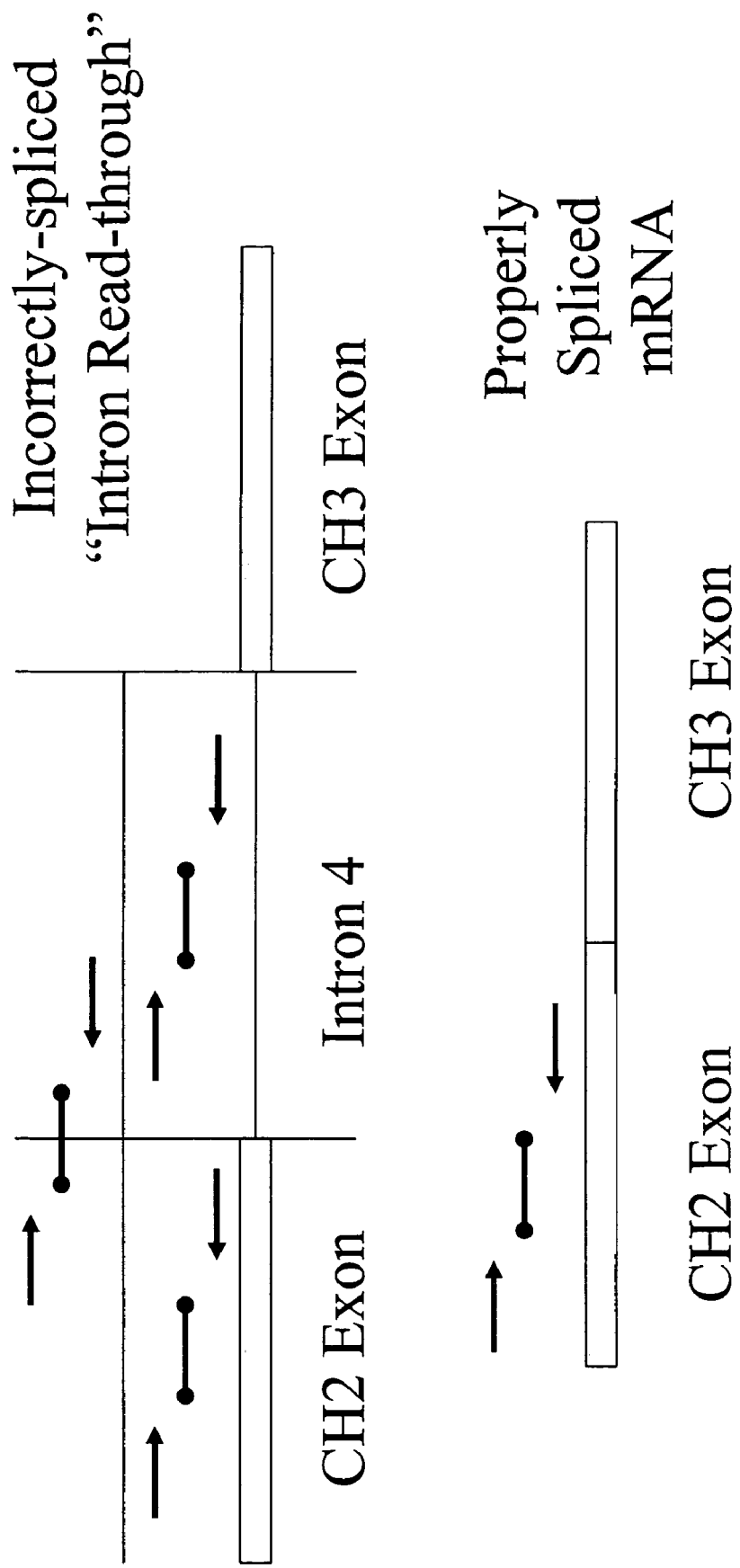
FIG. 3 is a schematic representation of the quantitative-polymerase chain reaction (Q-PCR) probes used to evaluate total levels of 3D6 heavy chain gene transcription (levels of CH2 containing mRNA transcript) and levels of intron 4 read-through transcription.

In order to quantify the relative amount of aberrant transcript formed due to intron read through, a quantitative PCR assay was designed. The approach for evaluating IRT transcription is graphically outlined in FIG. 3. Specifically, a quantitative PCR assay was devised using a TaqMan™ system, in which PCR amplification was employed to quantitate nucleic acid species of interest. Three probe-primer sets were designed to determine the fraction of intron read-through mRNA being produced. The first probe-primer set was designed to quantitate the level of transcription of sequence of an exon in natural operative association with an intron of interest. In the case of the 3D6 heavy chain expression cassette, mRNA species containing the 3D6 second constant heavy chain (CH2) exon was targeted. This provided a measure of total 3D6 mRNA production. The second probe primer set bridged the intron and exon in operative association, here the CH2 exon—fourth intron interface of the 3D6 expression cassette. Amplification derived from this probe primer set indicated the presence of intron read-through transcript containing the 5' splice donor sequence as well as sequence bridging the CH2 exon and intron 4. The third probe-primer set targeted sequence of the fourth intron. This probe set provided quantification of the fraction of incorrectly spliced RNA comprising internal intron 4 sequence.

Figure 4:
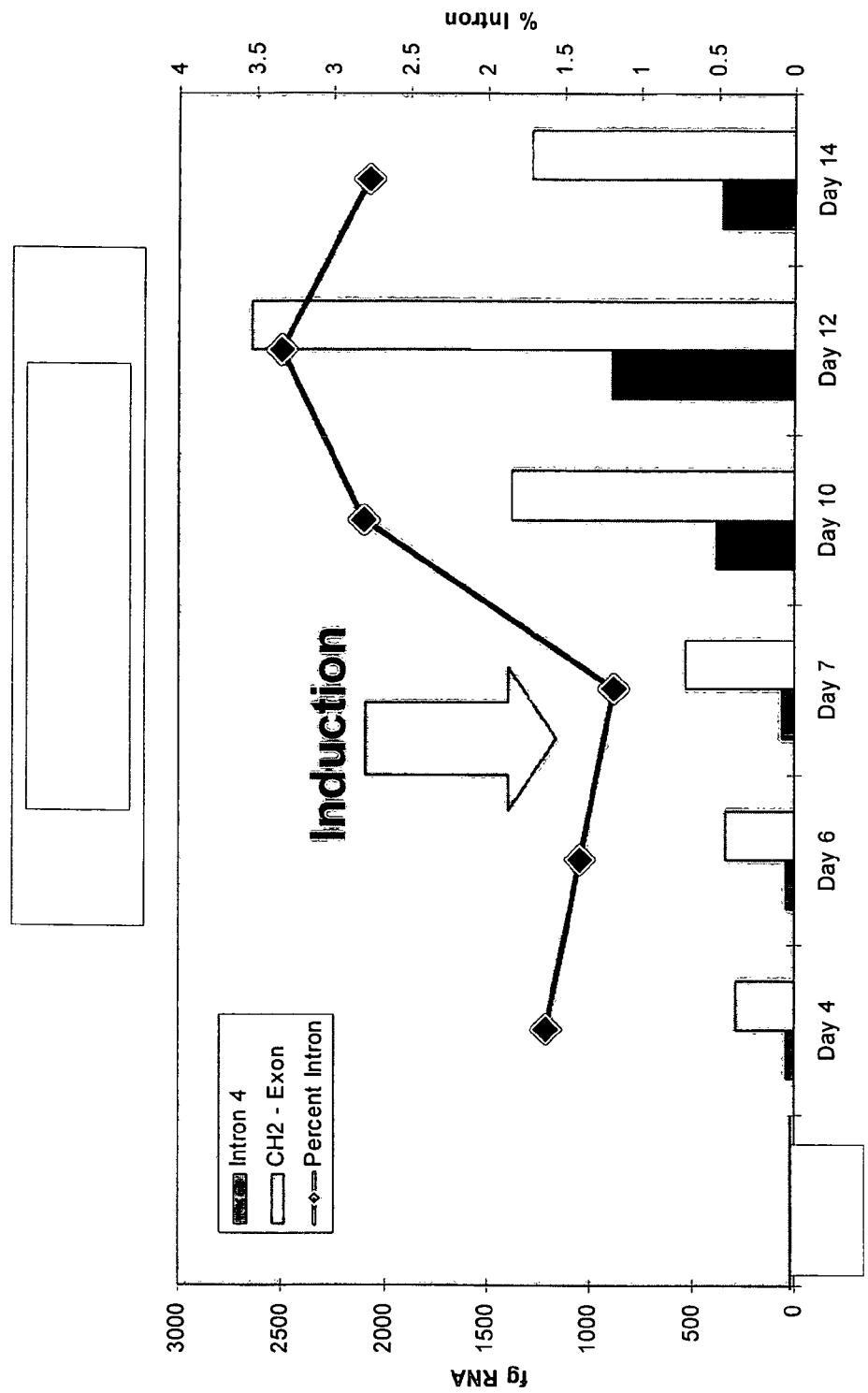
FIG. 4 is a bar graph demonstrating the increased accumulation of intron 4 containing transcripts in response to time in culture and protein expression induction.

FIG. 4 shows the results of the Q-PCR assay using the probe primer sets as described. Briefly, CHO cells containing the stably integrated expression vector were seeded and maintained in culture for two weeks. At day seven the cultures were induced to increase protein expression. During the course of the experiment, samples of the cell culture were lysed and RNA content evaluated in assays using probe and primer sets specific for the CH2 exon or specific for intron as described in the preceding paragraph. The chart demonstrates a low level of incorrectly spliced RNA product prior to induction and an increasing percentage of intron 4 containing RNA over time post-induction. This method of Q-PCR described here predicts the likelihood that a particular expression cassette containing introns and exons in naturally operative association will yield intron read through by-products.

While details for quantifying IRT of the 3D6 antibody expression system are explicitly provided, the technique can be implemented in any protein expression system wherein the potential of IRT exists. This novel approach is, therefore, especially useful for evaluating whether the vectors of this invention (described in detail below) should be adopted for a particular protein of interest such that the production of unwanted IRT polypeptide by-products are avoided. When IRT transcription is in an abundance of greater than about 0.1%-1%, vectors employing altered natural operative association can be employed to express the desired protein. It will be readily apparent to one of skill in the art that the methods for detecting intron-read through mRNA and, hence, predicting intron read-through polypeptides is applicable to any protein expression system wherein splicing events occur. For example the system may be used with any eukaryotic cell system, e.g. Saccharomyces, Drosophila, mouse, monkey, rabbit, rat, or human cell based systems.

Example 2

Vectors With Introns and Exons Having Modified Natural Operative Association

Figure 5:
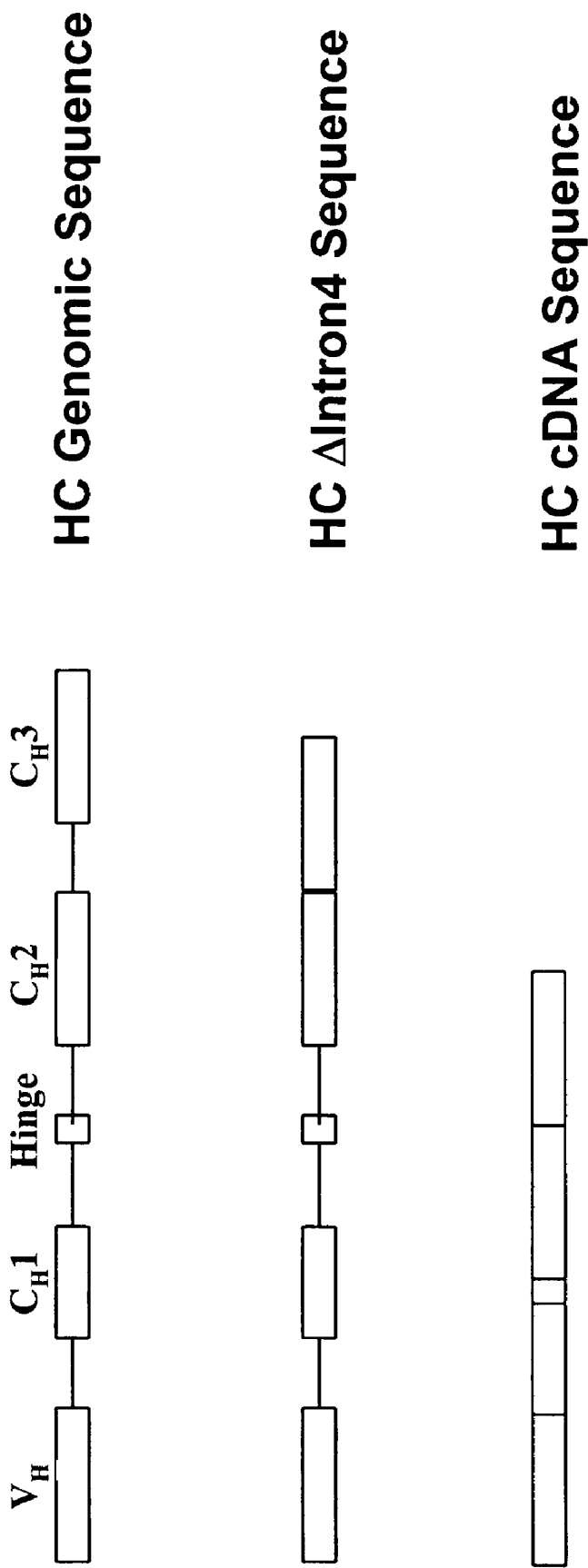
FIG. 5 provides drawings of the genomic arrangement of 3D6 introns and exons and the modified arrangement used in an expression vector developed to resolve intron read through transcription.

Expression vectors were devised wherein the natural operative association of the introns and exons were modified. Two exemplary vectors sequences are shown in FIG. 5. This figure illustrates expression constructs developed to resolve the problem of intron read-through by-products. The top panel graphically depicts the genomic, intronic-exonic, organization of a generic antibody heavy chain containing the exons for a variable region ($V_H$), three constant regions ($C_H1$, $C_H2$, $C_H3$) and a hinge region. The middle and bottom drawings describe modifications to the genomic sequence incorporated into expression vectors which eliminated intron read through heavy chain by-products.

Figure 6:
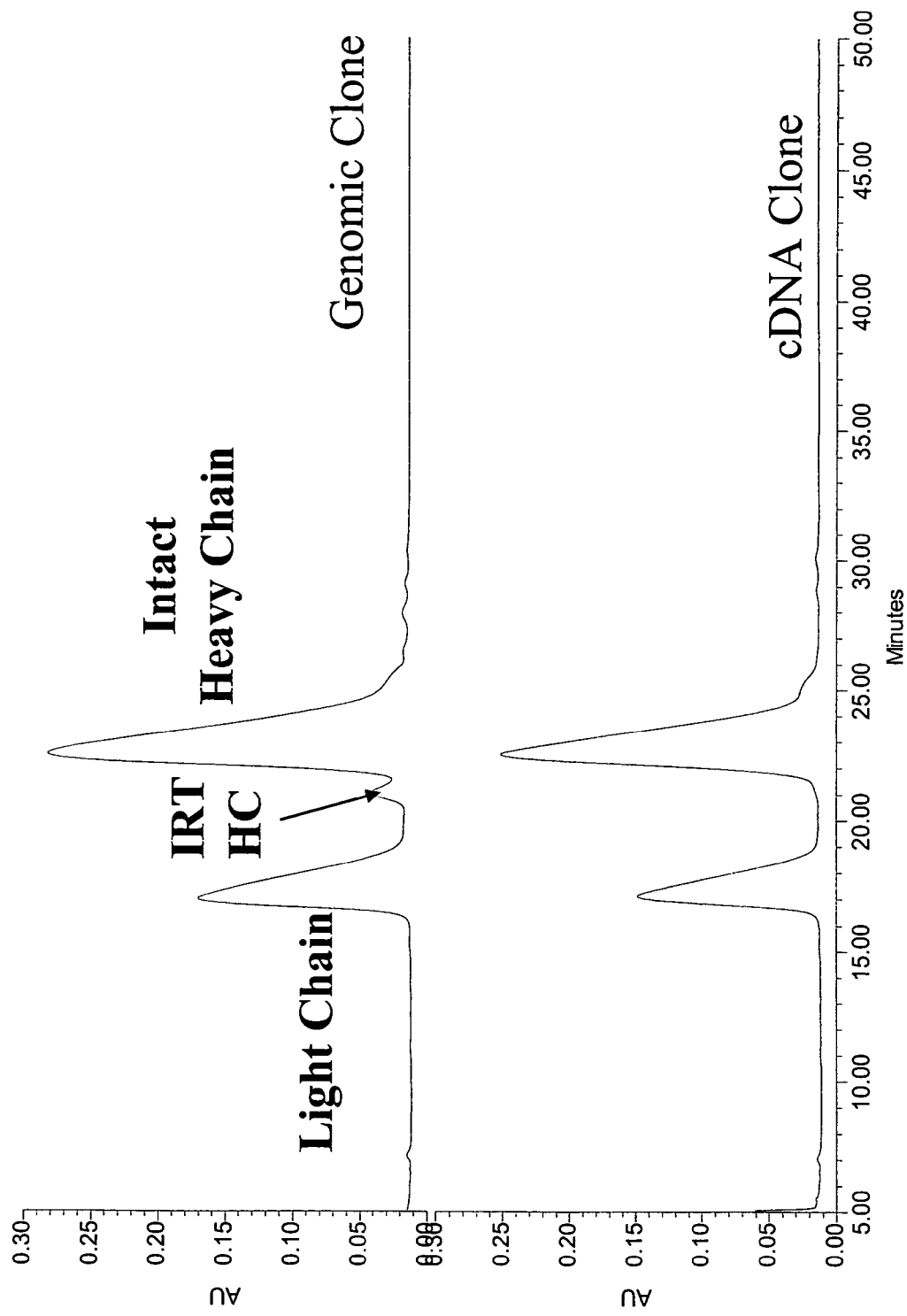
FIG. 6 shows reverse-phase high-performance liquid chromatography (RP-HPLC) chromatograms demonstrating the lack of intron read through heavy chain by-products in a cell line transformed with modified expression vectors.
Figure 7:
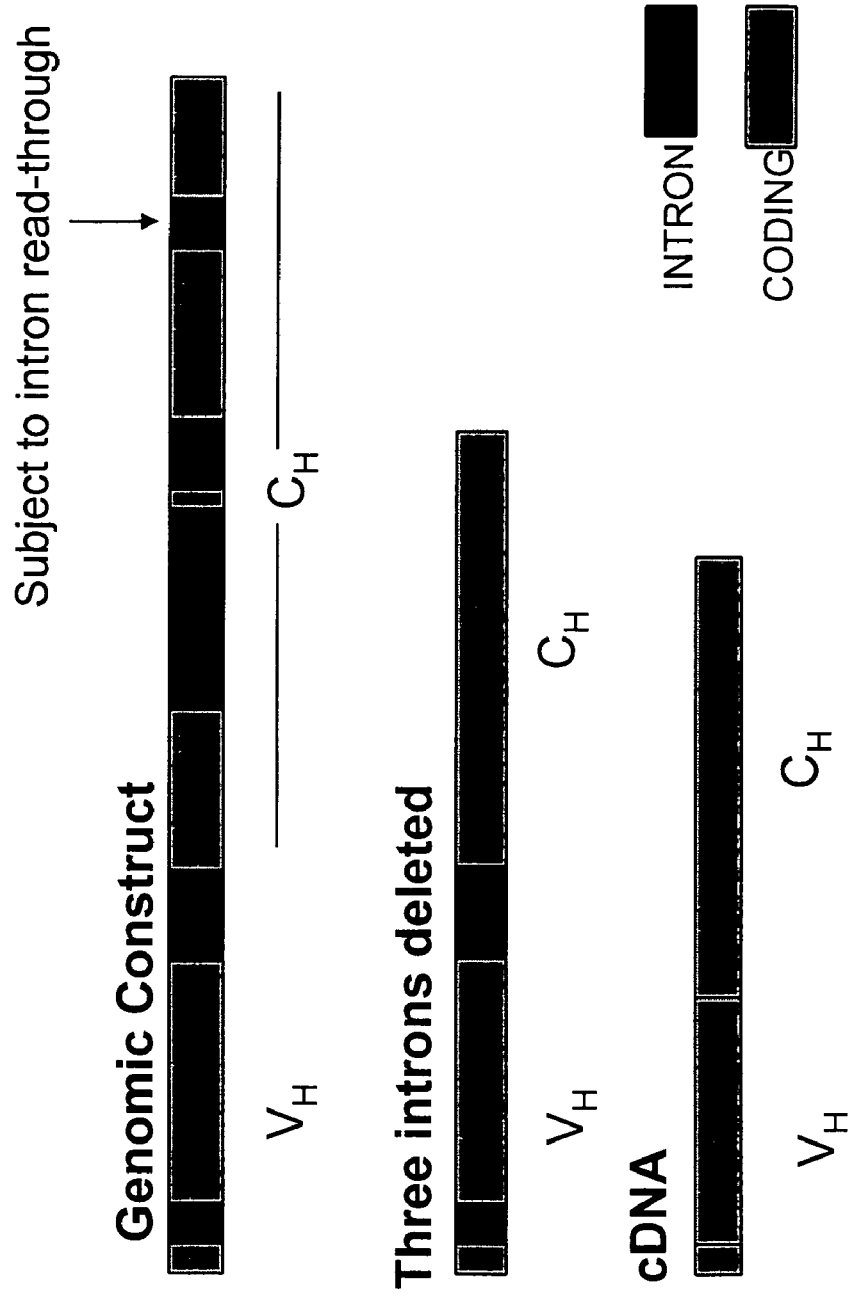
FIG. 7 depicts the arrangement of introns and exons in a heavy chain genomic construct, a construct, the construct with the last three intronic sequences deleted, and the cDNA construct containing no introns.

CHO cells expressing the 3D6 light chain were transformed with either the complete genomic heavy chain sequence of the 3D6 antibody or transformed with modified 3D6 heavy chain expression vectors wherein the natural operative association of introns and exons were modified. The cells were cultured using standard techniques for the purpose of protein expression as described in the Materials and Methods. Antibodies were purified from conditioned supernatant and subsequently fractionated using denaturing reverse phase (RP) HPLC (FIG. 6). The columns were run such that heavy and light chain constituents of the antibody were resolved.

In the top trace, representing the fractionation of a 3D6 genomic clone protein preparation, the heavy and light chains peaks are readily apparent. In addition, a small peak can be discerned fractionating between the heavy and light chain corresponding to heavy chain intron read-through product.

The bottom trace is an example of an expression system in which the problem of intron read-through has been reduced. As in the top trace, light chain and heavy chain peaks are clearly present, however, the level of IRT has been reduced to below the limit of detection. The finding has been extended to other vectors in which the natural operative association of exons and introns have been altered. For example, the HCΔIntron 4 sequence described in FIG. 5 similarly reduces IRT to undetectable levels.

Example 3

Origin and Description of the Anti-5T4 Coding Sequence

Anti-5T4 H8 was obtained as a mouse monoclonal antibody against soluble 5T4. The anti-5T4 H8 antibody was humanized by CDR grafting (VH, DP75 germline framework; VL DPK24 germline framework) and the variable regions were subcloned into vectors containing human IgG4 heavy chain constant domain (for VH domain) or human kappa light chain constant domain (VL domain) as appropriate. The humanized antibody is referred to as huH8. The hinge stabilizing mutation, Ser 241 to Pro, was introduced into the human IgG4. Sequences encoding huH8 heavy and light chain were ligated into expression vectors driven by the mouse CMV enhancer/promoter and containing the selectable marker genes dihydrofolate reductase (heavy chain expression vector) or neomycin resistance (light chain expression vector).

Example 4

Intron Removal Increases Protein Expression

To determine the effect of intron removal on antibody expression, expression constructs of several antibodies were created with differing numbers of introns. Variable regions of three different antibodies, 12A11v3.1, 356A11 and huH8, were each stably expressed in CHO cells with three constant region expression constructs containing genomic sequence, cDNA sequence, and genomic sequence with three introns deleted (i.e., intron between CH1 and hinge region, intron between the hinge region and CH2, and intron between CH2 and CH3). For constructs that gave poor expression, such as 12A11v3.1 and huH8, removal of the three introns or all introns, i.e., cDNA, gave a significant increase in antibody expression. More specifically, about a five-fold increase in expression was detected in the three-intron deleted construct for 12A11v3.1 compared to the genomic sequence. The 12A11v3.1 construct having the cDNA sequence showed over a six-fold increase in expression relative to the genomic sequence. The increased expression in CHO cells for huH8 antibodies was almost four-fold and nine-fold for the three-intron deleted and the cDNA construct, respectively, compared to the genomic sequence. Typically, well expressed antibodies did not show a significant change in CHO-cell expression between the intron-deleted sequences and the genomic sequences.

Although the foregoing invention has been described in detail for purposes of clarity of understanding, it will be obvious that certain modifications may be practiced within the scope of the appended claims. All publications and patent documents cited herein, as well as text appearing in the figures and sequence listing, are hereby incorporated by reference in their entirety for all purposes to the same extent as if each were so individually denoted.

We claim:

1. A purified nucleic acid molecule comprising a nucleotide sequence having one or more intron and exon sequences, wherein at least one intron sequence is deleted compared to the naturally-occurring genomic sequence and wherein the exon sequence comprises one or more of a second constant region ($C_H2$) exon or a third constant region ($C_H3$) exon, thereby reducing a mis-spliced or an intron read-through (IRT) by-product, and wherein said nucleotide sequence encodes an antibody heavy chain or a fragment thereof.

2. A purified nucleic acid molecule comprising a nucleotide sequence comprising one or more intron and exon sequences, wherein at least three intron sequences are deleted compared to the naturally-occurring genomic sequence and wherein the exon sequence comprises one or more of a second constant region ($C_H2$) exon or a third constant region ($C_H3$) exon, thereby enhancing protein expression, and wherein said nucleotide sequence encodes an antibody heavy chain or a fragment thereof.

3. The purified nucleic acid molecule of claim 1, wherein the antibody heavy chain or fragment thereof comprises one or more of a heavy chain variable region, a hinge region, a first constant region ($C_H1$), a second constant region ($C_H2$), or a third constant region ($C_H3$) of a human immunoglobulin G subtype, or a mutated form thereof.

4. The purified nucleic acid molecule of claim 2, wherein the antibody heavy chain or fragment thereof comprises one or more of a heavy chain variable region, a first constant region ($C_H1$), a second constant region ($C_H2$), or a third constant region ($C_H3$) of a human immunoglobulin G subtype, or a mutated form thereof.

5. The purified nucleic acid molecule of claim 3, wherein the immunoglobulin G subtype is a human IgG1 or human IgG4, or a mutated form thereof.

6. The purified nucleic acid molecule of claim 4, wherein the immunoglobulin G subtype is a human IgG1 or human IgG4, or a mutated form thereof.

7. The purified nucleic acid molecule of claim 3, wherein an intron between the CH2 region and the CH3 region of the immunoglobulin heavy chain constant region is deleted.

8. The purified nucleic acid molecule of claim 4, wherein an intron between the $C_H1$ region and the hinge region, an intron between the hinge region and the $C_H2$ region, and an intron between the $C_H2$ region and the $C_H3$ region of the immunoglobulin heavy chain constant region are deleted.

9. The purified nucleic acid molecule of claim 3, wherein the nucleic sequence encoding the heavy chain hinge region, and the first, second and third constant regions comprises a sequence at least 95% identical to the nucleotide sequence shown in FIG. 8 (SEQ ID NO:1), or at least 95% identical to the nucleotide sequence shown in FIG. 9 (SEQ ID NO:3).

10. The purified nucleic acid molecule of claim 4, wherein the nucleic sequence encoding the heavy chain hinge region, and the first, second and third constant regions comprises a sequence at least 95% identical to the nucleotide sequence shown in FIG. 8 (SEQ ID NO:1), or at least 95% identical to the nucleotide sequence shown in FIG. 9 (SEQ ID NO:3).

11. The purified nucleic acid molecule of claim 7, wherein the deletion of the intron between $C_H2$ and $C_H3$ corresponds to nucleotides between 1409 to 1505 of human IgG1 as shown in FIG. 8 (SEQ ID NO:1), or about nucleotides 1401 to 1497 of human IgG4 as shown in FIG. 9 (SEQ ID NO:3).

12. The purified nucleic acid molecule of claim 8, wherein the deletion of the intron between $C_H2$ and $C_H3$ corresponds to nucleotides between 1409 to 1505 of human IgG1 as shown in FIG. 8 (SEQ ID NO:1), or about nucleotides 1401 to 1497 of human IgG4 as shown in FIG. 9 (SEQ ID NO:3).

13. The purified nucleic acid molecule of claim 8, wherein the deletion of the intron between $C_H1$ and the hinge region corresponds to about nucleotides 525 to 915 of human IgG1 as shown in FIG. 8 (SEQ ID NO:1), or about nucleotides 525 to 916 of human IgG4 as shown in FIG. 9 (SEQ ID NO:3).

14. The purified nucleic acid molecule of claim 8, wherein the deletion of the intron between the hinge region and $C_H2$ corresponds to about nucleotides 961 to 1078 of human IgG1 as shown in FIG. 8 (SEQ ID NO:1), or about nucleotides 953 to 1070 of human IgG4 as shown in FIG. 9 (SEQ ID NO:3).

15. A purified nucleic acid molecule comprising a nucleotide sequence encoding human IgG1, wherein said nucleotide sequence is at least 90% identical to the sequence shown in FIG. 10 (SEQ ID NO:5), or at least 90% identical to the sequence shown in FIG. 11 (SEQ ID NO:6).

16. A purified genomic nucleotide sequence encoding a human IgG1 or IgG4 heavy chain constant region, or a mutated form thereof, wherein said nucleotide sequence lacks at least one intron present in the naturally-occurring genomic sequence, and wherein said intron facilitates intron-read through.

17. A purified nucleic acid molecule comprising a nucleotide sequence represented by the formula:

$V_H$-Int1-$C_H1$-Int2-Hinge-Int3-$C_H2$-$C_H3$, wherein $V_H$ is a nucleotide sequence encoding a heavy chain variable region;

$C_H1$, $C_H2$, and $C_H3$ are nucleotide sequences encoding a heavy chain constant region, wherein the heavy chain constant region is a human immunoglobulin G heavy chain constant region or a mutated form thereof;

Hinge is a nucleotide sequence encoding hinge region of the heavy chain constant region; and Int1, Int2, and Int3 are introns from a heavy chain genomic sequence.

18. A purified nucleic acid molecule comprising a nucleotide sequence represented by the formula:

$V_H$-Int1-$C_H1$-Hinge-$C_H2$-$C_H3$, wherein $V_H$ is a nucleotide sequence encoding a heavy chain variable region;

$C_H1$, $C_H2$, and $C_H3$ are nucleotide sequences encoding the corresponding heavy chain constant region, wherein the heavy chain constant region is a human immunoglobulin G heavy chain constant region or a mutated form thereof;

Hinge is a nucleotide sequence encoding hinge region of the heavy chain constant region; and Int1 is an intron from a heavy chain genomic sequence.

19. An expression vector comprising the nucleic acid molecule of claim 1 or 3.

20. An expression vector comprising the nucleic acid molecule of claim 2 or 4.

21. A cultured host cell comprising the expression vector of claim 19.

22. A cultured host cell comprising the expression vector of claim 20.

23. A method of expressing, in a mammalian host cell, a recombinant antibody or fragment thereof substantially free of an intron read-through (IRT) product, comprising;
   identifying an IRT product in a nucleic acid sample from the host cell;
   introducing the purified nucleic acid molecule of claim 3 into the host cell;
   culturing said host cell under conditions that allow expression of the recombinant antibody or fragment thereof, thereby producing a culture of host cells; and
   obtaining the recombinant antibody or fragment thereof from the culture of host cells.

24. A method for enhancing expression of a recombinant antibody or fragment thereof, comprising:
   introducing the purified nucleic acid molecule of claim 4, and a nucleotide sequence encoding a light chain variable region and a constant region into a mammalian host cell;
   culturing said host cell under conditions that allow expression of the recombinant antibody, thereby producing a culture of host cells; and
   obtaining the recombinant antibody from the culture of host cells.

25. A method for producing a recombinant antibody or fragment thereof substantially devoid of intron read-through (IRT) heavy chain by-product, comprising:
   culturing a mammalian host cell comprising the purified nucleic acid molecule of claim 3 and a nucleic acid encoding an antibody light chain, under conditions such that the heavy and light chains are expressed.

26. The purified nucleic acid molecule of claim 1 or 2, wherein the antibody heavy chain or fragment thereof encoded by the purified nucleic acid expressed in a CHO cell line at least two fold higher than the expression of the antibody heavy chain or fragment thereof encoded by the naturally-occurring genomic sequence.

27. The purified nucleic acid molecule of claim 26, wherein the antibody heavy chain or fragment thereof comprises one or more of a heavy chain variable region, a hinge region, a first constant region ($C_H1$), a second constant region ($C_H2$), or a third constant region ($C_H3$) of an immunoglobulin.

28. The purified nucleic acid molecule of claim 27, wherein the immunoglobulin is selected from the group consisting of IgG1, IgG3, and IgG4.

29. The purified nucleic acid molecule of claim 3 or 4, wherein the antibody heavy chain or fragment thereof comprises the heavy chain variable region, the hinge region, the first constant region ($C_H1$), the second constant region ($C_H2$), and the third constant region ($C_H3$) of the human immunoglobulin, or mutated form thereof.

30. The purified nucleic acid molecule of claim 3 or 4, wherein the mutated form of the antibody heavy chain or fragment thereof results in one or more of: increased stability, reduced effector function, reduced complement fixation, reduced glycosylation, relative to the naturally-occurring form.

31. The purified nucleic acid molecule of claim 1 or 2, wherein the nucleic acid molecule is modified by one or more of: rearranging the intron/exon configuration; deleting a portion of one or more introns; or replacing an intron or portion thereof with a heterologous intron sequence, such that when expressed enhanced protein expression and/or reduction or elimination of mis-spliced or intron read-through (IRT) by product occurs.

32. The purified nucleic acid molecule of claim 1 or 2, wherein the exon sequences comprise a heavy chain variable region exon, a hinge region exon, a first constant region ($C_H1$) exon, a second constant region ($C_H2$) exon, and a third constant region ($C_H3$) exon of a human immunoglobulin G subtype, or a mutated form thereof.

33. The purified nucleic acid molecule of claim 1 or 2, wherein the intron sequence between the $C_H2$ and $C_H3$ exons is deleted.

34. The purified nucleic acid molecule of claim 1 or 2, further comprising one or more deletions of the intron sequences between wherein $C_H1$ and the hinge region, or between the hinge region and $C_H2$.

35. A cultured host cell comprising the nucleic acid molecule of claim 1 or 2, wherein the host cell is transiently or stably transfected with said nucleic acid molecule.

36. The host cell of claim 35, wherein the host cell is cultured in large-scale.

37. The host cell of claim 35, wherein the host cell is a lymphocytic cell line or a COS cell line.

38. The host cell of claim 37, wherein the host cell is a COS cell line.

* * * * *

SEQUENCE LISTING

```
<160> NUMBER OF SEQ ID NOS: 9

<210> SEQ ID NO 1
<211> LENGTH: 1828
<212> TYPE: DNA
<213> ORGANISM: Homo sapiens
<220> FEATURE:
<221> NAME/KEY: intron
<222> LOCATION: (1)...(230)
<220> FEATURE:
<221> NAME/KEY: exon
<222> LOCATION: (231)...(524)
<220> FEATURE:
<221> NAME/KEY: intron
<222> LOCATION: (525)...(915)
<220> FEATURE:
<221> NAME/KEY: exon
<222> LOCATION: (916)...(960)
<220> FEATURE:
<221> NAME/KEY: intron
<222> LOCATION: (961)...(1078)
<220> FEATURE:
<221> NAME/KEY: exon
<222> LOCATION: (1079)...(1408)
<220> FEATURE:
<221> NAME/KEY: intron
<222> LOCATION: (1409)...(1505)
<220> FEATURE:
<221> NAME/KEY: exon
<222> LOCATION: (1506)...(1828)

<400> SEQUENCE: 1
gtgagtcctg tcgactctag agctttctgg ggcaggccag gcctgacttt ggctggggc      60 agggagggg  ctaaggtgac gcaggtggcg ccagccaggc gcacacccaa tgcccatgag    120
```

-continued

```
cccagacact ggacgctgaa cctcgcggac agttaagaac ccaggggcct ctgcgccctg    180
ggcccagctc tgtcccacac cgcggtcaca tggcaccacc tctcttgcag cctccaccaa    240
gggcccatcg tcttcccccc tggcaccctc ctccaagagc acctctgggg gcacagcggc    300
cctgggctgc ctggtcaagg actacttccc cgaaccggtg acggtgtcgt ggaactcagg    360
cgccctgacc agcggcgtgc acaccttccc ggctgtccta cagtcctcag gactctactc    420
cctcagcagc gtggtgaccg tgccctccag cagcttgggc acccagacct acatctgcaa    480
cgtgaatcac aagcccagca acaccaaggt ggacaagaaa gttggtgaga ggccagcaca    540
gggagggagg gtgtctgctg gaagccaggc tcagcgctcc tgcctggacg catcccggct    600
atgcagtccc agtccagggc agcaaggcag gccccgtctg cctcttcacc cggaggcctc    660
tgcccgcccc actcatgctc agggagaggg tcttctggct ttttcccag gctctgggca    720
ggcacaggct aggtgcccct aacccaggcc ctgcacacaa aggggcaggt gctgggctca    780
gacctgccaa gagccatatc cgggaggacc ctgcccctga cctaagccca ccccaaaggc    840
caaactctcc actccctcag ctcggacacc ttctctcctc ccagattcca gtaactccca    900
atcttctctc tgcagagccc aaatcttgtg acaaaactca cacatgccca ccgtgcccag    960
gtaagccagc ccaggcctcg ccctccagct caaggcggga caggtgccct agagtagcct   1020
gcatccaggg acaggcccca gccgggtgct gacacgtcca cctccatctc ttcctcagca   1080
cctgaactcc tggggggacc gtcagtcttc ctcttccccc caaaacccaa ggacaccctc   1140
atgatctccc ggacccctga ggtcacatgc gtggtggtgg acgtgagcca cgaagaccct   1200
gaggtcaagt tcaactggta cgtggacggc gtggaggtgc ataatgccaa gacaaagccg   1260
cgggaggagc agtacaacag cacgtaccgt gtggtcagcg tcctcaccgt cctgcaccag   1320
gactggctga atggcaagga gtacaagtgc aaggtctcca acaaagccct cccagccccc   1380
atcgagaaaa ccatctccaa agccaaaggt gggacccgtg gggtgcgagg ccacatggac   1440
cagaggccgg ctcggcccac cctctgccct gagagtgacc gctgtaccaa cctctgtccc   1500
tacagggcag ccccgagaac acaggtgta cccctgcccc catcccggg aggagatgac   1560
caagaaccag gtcagcctga cctgcctggt caaaggcttc tatcccagcg acatcgccgt   1620
ggagtgggag agcaatgggc agccggagaa caactacaag accacgcctc ccgtgctgga   1680
ctccgacggc tccttcttcc tctatagcaa gctcaccgtg gacaagagca ggtggcagca   1740
ggggaacgtc ttctcatgct ccgtgatgca tgaggctctg cacaaccact acacgcagaa   1800
gagcctctcc ctgtccccgg gtaaatga                                      1828
```

<210> SEQ ID NO 2
<211> LENGTH: 330
<212> TYPE: PRT
<213> ORGANISM: Homo sapiens

<400> SEQUENCE: 2

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 1820
<212> TYPE: DNA
<213> ORGANISM: Artificial Sequence
<220> FEATURE:
<223> OTHER INFORMATION: Mutant from human IgG4
<220> FEATURE:
<221> NAME/KEY: intron
<222> LOCATION: (1)...(230)
<220> FEATURE:
<221> NAME/KEY: exon
<222> LOCATION: (231)...(524)
<220> FEATURE:
<221> NAME/KEY: intron
<222> LOCATION: (525)...(916)
<220> FEATURE:
<221> NAME/KEY: exon
<222> LOCATION: (916)...(952)
<220> FEATURE:
<221> NAME/KEY: intron
<222> LOCATION: (953)...(1070)
<220> FEATURE:
<221> NAME/KEY: exon
<222> LOCATION: (1071)...(1400)
<220> FEATURE:
<221> NAME/KEY: intron
<222> LOCATION: (1401)...(1497)
```

```
<220> FEATURE:
<221> NAME/KEY: exon
<222> LOCATION: (1498)...(1820)

<400> SEQUENCE: 3
gtgagtcctg tcgactctag agctttctgg ggcaggccag gcctgacttt ggctgggggc      60
agggaggggg ctaaggtgac gcaggtggcg ccagccaggc gcacacccaa tgcccatgag     120
cccagacact ggacgctgaa cctcgcggac agttaagaac ccaggggcct ctgcgccctg     180
ggcccagctc tgtcccacac cgcggtcaca tggcaccacc tctcttgcag cctccaccaa     240
gggcccatcg gtcttccccc tggcgccctg ctccaggagc acctccgaga gcacagcggc     300
cctgggctgc ctggtcaagg actacttccc cgaaccggtg acggtgtcgt ggaactcagg     360
cgccctgacc agcggcgtgc acaccttccc ggctgtccta cagtcctcag gactctactc     420
cctcagcagc gtggtgaccg tgccctccag cagcttgggc acgaagacct acacctgcaa     480
tgtagatcac aagcccagca acaccaaggt ggacaagaga gttggtgaga ggccagcaca     540
gggagggagg gtgtctgctg gaagccaggc tcagccctcc tgcctggacg caccccggct     600
gtgcagcccc agcccagggc agcaaggcag gccccatctg tctcctcacc tggaggcctc     660
tgaccacccc actcatgctc agggagaggg tcttctggat ttttccacca ggctccgggc     720
agccacaggc tggatgcccc taccccaggc cctgcgcata caggggcagg tgctgcgctc     780
agacctgcca agagccatat ccgggaggac cctgcccctg acctaagccc accccaaagg     840
ccaaactctc cactccctca gctcagacac ctttctctcct cccagatctg agtaactccc     900
aatcttctct ctgcagagtc caaatatggt cccccatgcc accatgccc aggtaagcca     960
acccaggcct cgccctccag ctcaaggcgg gacaggtgcc ctagagtagc ctgcatccag    1020
ggacaggccc cagccgggtg ctgacgcatc cacctccatc tcttcctcag cacctgagtt    1080
cctgggggga ccatcagtct tcctgttccc cccaaaaccc aaggacactc tcatgatctc    1140
ccggacccct gaggtcacgt gcgtggtggt ggacgtgagc caggaagacc ccgaggtcca    1200
gttcaactgg tacgtggatg gcgtggaggt gcataatgcc aagacaaagc cgcgggagga    1260
gcagttcaac agcacgtacc gtgtggtcag cgtcctcacc gtcctgcacc aggactggct    1320
gaacggcaag gagtacaagt gcaaggtctc caacaaaggc ctcccgtcct ccatcgagaa    1380
aaccatctcc aaagccaaag gtgggaccca cggggtgcga gggccacatg gacagaggtc    1440
agctcggccc accctctgcc ctgggagtga ccgctgtgcc aacctctgtc cctacagggc    1500
agccccgaga gccacaggtg tacaccctgc ccccatccca ggaggagatg accaagaacc    1560
aggtcagcct gacctgcctg gtcaaaggct tctaccccag cgacatcgcc gtggagtggg    1620
agagcaatgg gcagccggag aacaactaca agaccacgcc tcccgtgctg gactccgacg    1680
gctccttctt cctctacagc aggctaaccg tggacaagag caggtggcag gaggggaatg    1740
tcttctcatg ctccgtgatg catgaggctc tgcacaacca ctacacacag aagagcctct    1800
ccctgtctct gggtaaatga                                                 1820

<210> SEQ ID NO 4
<211> LENGTH: 304
<212> TYPE: PRT
<213> ORGANISM: Artificial Sequence
<220> FEATURE:
<223> OTHER INFORMATION: Mutant from human IgG4

<400> SEQUENCE: 4

Ala Ser Thr Lys Gly Pro Ser Val Phe Pro Leu Ala Pro Cys Ser Arg
```

```
            1               5                  10                 15
Ser Thr Ser Glu Ser Thr Ala Ala Leu Gly Cys Leu Val Lys Asp Tyr
                20                 25                 30

Phe Pro Glu Pro Val Thr Val Ser Trp Asn Ser Gly Ala Leu Thr Ser
                35                 40                 45

Gly Val His Thr Phe Pro Ala Val Leu Gln Ser Ser Gly Leu Tyr Ser
                50                 55                 60

Leu Ser Ser Val Val Thr Val Pro Ser Ser Ser Leu Gly Thr Lys Thr
65                  70                 75                 80

Tyr Thr Cys Asn Val Asp His Lys Pro Ser Asn Thr Lys Val Asp Lys
                85                 90                 95

Arg Val Glu Ser Lys Tyr Gly Pro Pro Cys Pro Pro Cys Pro Leu Leu
                100                105                110

Gly Gly Pro Ser Val Phe Leu Phe Pro Pro Lys Pro Lys Asp Thr Leu
                115                120                125

Met Ile Ser Phe Asn Trp Tyr Val Asp Gly Val Glu Val His Asn Ala
                130                135                140

Lys Thr Lys Pro Arg Glu Glu Gln Phe Asn Ser Thr Tyr Arg Val Val
145                 150                155                160

Ser Val Leu Thr Val Leu His Gln Asp Trp Leu Asn Gly Lys Glu Tyr
                165                170                175

Lys Cys Lys Val Ser Asn Lys Gly Leu Pro Ser Ser Ile Glu Lys Thr
                180                185                190

Ile Ser Lys Ala Lys Gly Gln Pro Arg Glu Pro Gln Val Tyr Thr Leu
                195                200                205

Pro Pro Ser Gln Glu Glu Met Thr Lys Asn Gln Val Ser Leu Thr Cys
                210                215                220

Leu Val Lys Gly Phe Tyr Pro Ser Asp Ile Ala Val Glu Trp Glu Ser
225                 230                235                240

Asn Gly Gln Pro Glu Asn Asn Tyr Lys Thr Thr Pro Pro Val Leu Asp
                245                250                255

Ser Asp Gly Ser Phe Phe Leu Tyr Ser Arg Leu Thr Val Asp Lys Ser
                260                265                270

Arg Trp Gln Glu Gly Asn Val Phe Ser Cys Ser Val Met His Glu Ala
                275                280                285

Leu His Asn His Tyr Thr Gln Lys Ser Leu Ser Leu Ser Leu Gly Lys
                290                295                300

<210> SEQ ID NO 5
<211> LENGTH: 1731
<212> TYPE: DNA
<213> ORGANISM: Artificial Sequence
<220> FEATURE:
<223> OTHER INFORMATION: Modified nucleic acid sequence encoding human
      IgG1

<400> SEQUENCE: 5
gtgagtcctg tcgactctag agctttctgg ggcaggccag gcctgacttt ggctgggggc      60
agggaggggg ctaaggtgac gcaggtggcg ccagccaggc gcacacccaa tgcccatgag     120
cccagacact ggacgctgaa cctcgcggac agttaagaac caggggcct  ctgcgccctg     180 ggcccagctc tgtcccacac cgcggtcaca tggcaccacc tctcttgcag cctccaccaa     240
gggcccatcg gtcttccccc tggcaccctc ctccaagagc acctctgggg gcacagcggc     300
cctgggctgc ctggtcaagg actacttccc cgaaccggtg acggtgtcgt ggaactcagg     360
```

```
cgccctgacc agcggcgtgc acaccttccc ggctgtccta cagtcctcag gactctactc    420
cctcagcagc gtggtgaccg tgccctccag cagcttgggc acccagacct acatctgcaa    480
cgtgaatcac aagcccagca acaccaaggt ggacaagaaa gttggtgaga ggccagcaca    540
gggagggagg gtgtctgctg gaagccaggc tcagcgctcc tgcctggacg catcccggct    600
atgcagtccc agtccagggc agcaaggcag gccccgtctg cctcttcacc cggaggcctc    660
tgcccgcccc actcatgctc agggagaggg tcttctggct ttttccccag gctctgggca    720
ggcacaggct aggtgcccct aacccaggcc ctgcacacaa aggggcaggt gctgggctca    780
gacctgccaa gagccatatc cgggaggacc ctgcccctga cctaagccca cccaaaggc    840 caaactctcc actccctcag ctcggacacc ttctctcctc ccagattcca gtaactccca    900
atcttctctc tgcagagccc aaatcttgtg acaaaactca cacatgccca ccgtgcccag    960
gtaagccagc ccaggcctcg ccctccagct caaggcggga caggtgccct agagtagcct    1020
gcatccaggg acaggcccca gccgggtgct gacacgtcca cctccatctc ttcctcagca    1080
cctgaactcc tggggggacc gtcagtcttc ctcttccccc caaaacccaa ggacaccctc    1140
atgatctccc ggacccctga ggtcacatgc gtggtggtgg acgtgagcca cgaagaccct    1200
gaggtcaagt tcaactggta cgtggacggc gtggaggtgc ataatgccaa gacaaagccg    1260
cgggaggagc agtacaacag cacgtaccgt gtggtcagcg tcctcaccgt cctgcaccag    1320
gactggctga atggcaagga gtacaagtgc aaggtctcca acaaagccct cccagccccc    1380
atcgagaaaa ccatctccaa agccaaaggg cagccccgag aaccacaggt gtacaccctg    1440
cccccatccc gggaggagat gaccaagaac caggtcagcc tgacctgcct ggtcaaaggc    1500
ttctatccca gcgacatcgc cgtggagtgg gagagcaatg ggcagccgga gaacaactac    1560
aagaccacgc ctcccgtgct ggactccgac ggctccttct tcctctatag caagctcacc    1620
gtggacaaga gcaggtggca gcaggggaac gtcttctcat gctccgtgat gcatgaggct    1680
ctgcacaacc actacacgca gaagagcctc tccctgtccc cgggtaaatg a    1731
```

<210> SEQ ID NO 6
<211> LENGTH: 1213
<212> TYPE: DNA
<213> ORGANISM: Artificial Sequence
<220> FEATURE:
<223> OTHER INFORMATION: Modified nucleic acid sequence encoding
      human IgG4

<400> SEQUENCE: 6

```
gtgagtcctg tcgactctag agctttctgg ggcaggccag gcctgacttt ggctgggggc    60
agggaggggg ctaaggtgac gcaggtggcg ccagccaggc gcacacccaa tgcccatgag    120
cccagacact ggacgctgaa cctcgcggac agttaagaac caggggcct  ctgcgccctg    180 ggcccagctc tgtcccacac cgcggtcaca tggcaccacc tctcttgcag cctccaccaa    240
gggcccatcg gtcttccccc tggcgccctg ctccaggagc acctccgaga gcacagcggc    300
cctgggctgc ctggtcaagg actacttccc cgaaccggtg acggtgtcgt ggaactcagg    360
cgccctgacc agcggcgtgc acaccttccc ggctgtccta cagtcctcag gactctactc    420
cctcagcagc gtggtgaccg tgccctccag cagcttgggc acgaagacct acacctgcaa    480
tgtagatcac aagcccagca acaccaaggt ggacaagaga gttgagtcca aatatggtcc    540
cccatgccca ccatgcccag cacctgagtt cctggggga ccatcagtct tcctgttccc    600
cccaaaaccc aaggacactc tcatgatctc ccggaccct gaggtcacgt gcgtggtggt    660
```

```
ggacgtgagc caggaagacc ccgaggtcca gttcaactgg tacgtggatg gcgtggaggt    720
gcataatgcc aagacaaagc cgcgggagga gcagttcaac agcacgtacc gtgtggtcag    780
cgtcctcacc gtcctgcacc aggactggct gaacggcaag gagtacaagt gcaaggtctc    840
caacaaaggc ctcccgtcct ccatcgagaa aaccatctcc aaagccaaag ggcagccccg    900
agagccacag gtgtacaccc tgcccccatc ccaggaggag atgaccaaga accaggtcag    960
cctgacctgc ctggtcaaag gcttctaccc cagcgacatc gccgtggagt gggagagcaa   1020
tgggcagccg gagaacaact acaagaccac gcctcccgtg ctggactccg acggctcctt   1080
cttcctctac agcaggctaa ccgtggacaa gagcaggtgg caggagggga atgtcttctc   1140
atgctccgtg atgcatgagg ctctgcacaa ccactacaca cagaagagcc tctccctgtc   1200
tctgggtaaa tga                                                      1213

<210> SEQ ID NO 7
<211> LENGTH: 240
<212> TYPE: DNA
<213> ORGANISM: Artificial Sequence
<220> FEATURE:
<223> OTHER INFORMATION: Synthetically generated oligonucleotide

<400> SEQUENCE: 7
ggcaaggagt acaagtgcaa ggtctccaac aaagccctcc cagcccccat cgagaaaacc     60
atctccaaag ccaaaggtgg gacccgtggg gtgcgagggc acatggaca gaggccggct    120 cggcccaccc tctgccctga gagtgaccgc tgtaccaacc tctgtcccta cagggcagcc    180
ccgagaacca caggtgtaca ccctgccccc atcccgggag gagatgacca gaaccaggt    240

<210> SEQ ID NO 8
<211> LENGTH: 80
<212> TYPE: PRT
<213> ORGANISM: Artificial Sequence
<220> FEATURE:
<223> OTHER INFORMATION: Synthetically generated peptide

<400> SEQUENCE: 8

Gly Lys Glu Tyr Lys Cys Lys Val Ser Asn Lys Ala Leu Pro Ala Pro
 1               5                  10                  15

Ile Glu Lys Thr Ile Ser Lys Ala Lys Gly Gly Thr Arg Gly Val Arg
            20                  25                  30

Gly Pro His Gly Gln Arg Pro Ala Arg Pro Thr Leu Cys Pro Glu Ser
        35                  40                  45

Asp Arg Cys Thr Asn Leu Cys Pro Tyr Arg Ala Ala Pro Arg Thr Thr
    50                  55                  60

Gly Val His Thr Ala Pro Ile Pro Gly Gly Asp Asp Gln Glu Pro Cys
65                  70                  75                  80

<210> SEQ ID NO 9
<211> LENGTH: 47
<212> TYPE: PRT
<213> ORGANISM: Artificial Sequence
<220> FEATURE:
<223> OTHER INFORMATION: Synthetically generated peptide

<400> SEQUENCE: 9

Gly Lys Glu Tyr Lys Cys Lys Val Ser Asn Lys Ala Leu Pro Ala Pro
 1               5                  10                  15

Ile Glu Lys Thr Ile Ser Lys Ala Lys Gln Pro Arg Glu Pro Gln Val
            20                  25                  30
```

-continued

```
Tyr Thr Leu Pro Pro Ser Arg Glu Glu Met Thr Lys Asn Gln Val
     35                  40                  45
```